United States Patent [19]

Paños

[11] Patent Number: 5,763,259
[45] Date of Patent: Jun. 9, 1998

[54] BIO-METALLURGICAL PROCESS IN WHICH BIO-OXIDATION OF MINERAL COMPOUNDS IS PRODUCED

[75] Inventor: Nora Hilda Paños, San Juan, Argentina

[73] Assignee: Leaching S.R.L., Argentina

[21] Appl. No.: 103,257

[22] Filed: Aug. 9, 1993

Related U.S. Application Data

[63] Continuation-in-part of Ser. No. 788,271, Nov. 6, 1991, abandoned.

[30] Foreign Application Priority Data

Nov. 7, 1990 [AR] Argentina ................... 318.330

[51] Int. Cl.$^6$ ...................................................... C12P 3/00
[52] U.S. Cl. ................... 435/262; 435/264; 423/DIG. 17
[58] Field of Search ................................ 435/262, 264, 435/252.1; 423/DIG. 17

[56] References Cited

U.S. PATENT DOCUMENTS

| | | |
|---|---|---|
| 3,883,310 | 5/1975 | Killgore ................................ 23/283 |
| 4,729,788 | 3/1988 | Hutchins et al. ....................... 75/118 |
| 4,861,723 | 8/1989 | Madgavkan ............................ 435/262 |

OTHER PUBLICATIONS

Kulebakin,V.G. "Manometric Research on the Process of CuS Leaching" ISV 51B OTD AKAD SSSR Ser Biol Nauk (3) 1977 pp. 140–145.

Doepker, R. "Enhanced Heavy Metal Mobilization From Unsaturated Mine Tailings": Trans of Soc. for Mining Metallurgy and Exploration, vol. 288 1990 pp. 1801–1805.

P.T. Malakhova et al., "Improvement of the Efficiency of the Leaching of Copper from Balanced Sulfide Oresfrom Kal 'Makyr", Tsvetnye Metally/Non–Ferrous Metals, pp. 23–24. (1985).

A. Ballester, et al., "Microbiological Leaching of Copper From Lead Mattes", 2207b Metallurgical Transactions B, vol. 20B(1989) Dec., 1989, No. 6, Warrendale, PA, US, pp. 773–779.

Letter (in French) by Dr. Georges Cohen, Professor of the Buenos Aires University, dated Nov. 26, 1990 (along with Certified English Translation).

Corale L. Brierley, "The central role of bacteria in the leaching... application of novel methods of microbiological technology", Microbiological Mining. 247(2) pp. 42–51. (1982).

William W. Leathen, et al., "Ferrobacillus Ferrooxidans: A Chemosynthetic Autotrophic Bacterium", Mellon Institute, Pittsburgh, PA, (1956) vol. 72, pp. 700–704.

Olli H. Tuovinen et al., "Studies on the Growth of Thiobacillus Ferrooxidans", Arch. Mikrobiol. 89, 285–296 (1973), by Springer–Verlag 1973.

Melvin P. Silverman et al., "Studies On the Chemoautotrophic... Ferrooxidans", Department of Bacteriology and Botany, Syracuse University, Syracuse, New York, pp. 642–647. (1959).

Herbert L. Manning, "New Medium for Isolating Iron–Oxidizing and Heterotrophic Acidophilic Bacteria from Mine Drainage", Applied Microbiology, Dec. 1975, pp. 1010–1016, vol. 30, No. 6.

Arthur R. Colmer, et al., "The Role of Microoganisms in Acid Mine Drainage: A Preliminary Report", Agricultural Experiment Station (Scientific Paper No. 373), and Engineering Experiment Station, West Virginia University, Science, Sep. 19, 1947, pp. 253–256.

Olli H. Tuovinen, "Some Characteristics of Iron–Oxidizing Thiobacilli Isolated From Uranium Mine Leach Liquors", United Nations Environment Programme, pp. 56–63, Moscow, 1985 of metals from Ores, (24 May–25 Jun. 1982, Moscow–Sophia), pp. 56–62.

Stoyan N. Groudev, "Differences Between Strains Of Thiobacillus Ferrooxidans With Respect To Their Ability To Oxidize Sulphide Minerals", United Nations Environment Programme, pp. 83–96, Moscow, 1985.

G.I. Karvaiko et al., "Microorganisms And Their Significance Fro Biogeotechnology Of Metals", United Nations Environment Programme (UNEP), USSR Commission For UNEP, Biogeotechnology Of Metals Manual, pp. 10–86 (1988).

D. G. Lundgren, "Ore Leaching by Bacteria", Ann. Rev. Microbiol. 1980, 34:263–83, 1980.

V.K. Berry and L. E. Murr (1978), "Direct Observations Of Bacteria And Quantitative Studies Of Their . . . Copper–Bearing Waste", Metallurgical Applications of Bacterial Leaching and Related Microbiological Phenomena, 103–135.

Stoyan N. Groudev,, et al., (1978) "Observations On the Microflora In An Industrial Copper Dump Leaching Operation", Metallurgical Applications of Bacterial Leaching and Related Microbiological Phenomena, 253–274.

R. W. Lawrence, R. Branion and H. Ebner, Editors, Fundamental And Applied Biohydrometallurgy, Proceedings of The Sixth International Symposium on Biohydrometallurgy, Vancouver, B.C., Canada, Aug. 21–24, 1985, pp. 3–501.

*Primary Examiner*—Carolyn Paden
*Attorney, Agent, or Firm*—Cushman Darby & Cushman IP Group of Pillsbury Madison & Sutro, LLP

[57] ABSTRACT

The present invention relates to a process for bio-oxidating insoluble mineral compounds from ores comprising the steps of:

a) conditioning the ore with an acidic solution;

b) adding a microbial inoculum to the conditioned ore;

c) drying the ore until soluble bio-oxidized products in solid state are obtained, the solid products containing microbial colonies;

d) maintaining the ore into an adequate range of temperature for the employed microorganism, until the bio-oxidation is completed; and e) separating out the soluble bio-oxidized products in solid state by washing or by another suitable method.

12 Claims, 27 Drawing Sheets

1 cm

BIO-METALLURGICAL PROCESS IN WHICH BIO-OXIDATION OF MINERAL COMPOUNDS IS PRODUCED

The subject application is a Continuation-In-Part of U.S. patent application Ser. No. 07/788,271, filed on Nov. 6, 1991, now abandoned and is hereby incorporated in its entirety by reference.

BACKGROUND OF THE INVENTION

1. Technical Field of the Invention

The present invention relates to a process in which insoluble mineral compounds, which act as substrates for microorganisms, are bio-oxidized and thereby converted to soluble compounds. Thus, such bio-oxidation allows for solubilization and separation of the bio-oxidized products.

2. Background Information

"Biotechnology of metals" is the science of extracting metals from minerals, concentrates, rocks and solutions by the action of microorganisms or their metabolites at normal pressure and at a temperature of 5° to 100° C. One of its areas of technological development is biohydrometallurgy. This refers to the oxidation of sulphide minerals, elemental sulphur, ferrous iron and a number of reduced metals by acidophilus microorganisms which turns them into soluble, easily separable compounds. Optimization of this technology could advantageously compete with the conventional processes of extractive metallurgy.

By bacterial leaching, it is possible to oxidize the following sulfides: pyrite and marcasite ($FeS_2$), pyrrhotite (FeS), chalcopyrite ($CuFeS_2$), bornite ($Cu_5FeS_4$), covellite (CuS), chalcocite ($Cu_2S$), tetrahedrite ($Cu_8Sb_2S_7$), enargite ($3Cu_2S.As_2S_5$), molybdenite ($MoS_2$), sphalerite (ZnS), arsenopyrite (FeAsS), realgar (AsS), orpiment ($As_2S_3$), cobaltite (CoAsS), pentlandite $(Fe,Ni)_9 S_8$, violarite ($Ni_2FeS_4$), bravoite $(Ni,Fe)S_2$, millerite (NiS), polydymite ($Ni_3S_4$), antimonite ($Sb_2S_3$), marmatite (ZnS), galena (PbS), geocronite $Pb_5(Sb, As_2)S_8$, $Ga_2S_3$ and CuSe among others.

The above metal sulphides are included or disseminated in rocks, as they are found in nature. The rocks are of different origins, such as igneous rocks, sedimentary rocks or conglomerates. Some of these rocks, such as sedimentary or conglomerates, contain, on some occasions, carbon, as diamond or as amorphous carbon. The carbon may be combined with organic compounds, as in the case of coal. In most cases the valuable part of the ores is the metal sulphides with the rock considered as waste material. In the case of coal, the valuable material is the coal, and the metal sulphides are considered undesirable contaminants. In precious metals, ores or concentrates, the metal sulphides may also be considered undesirable contaminants.

Important activities in the mining industry are the extraction of the valuable metals from ores, the refining of coal from undesirable contaminants, or the purification of precious metals. In these three related cases, the metals are usually found as sulphides.

A normal practical procedure in the mining industry is to improve the metal grades by applying concentration processes. This concentration is done by the crushing the natural minerals to sizes of the same magnitude as the metal sulphide particles in order to liberate them from the rocks, for example, to 10 millimeters when the metal sulphides are of a medium size of 10 millimeters, or grinding the natural minerals, for example, to 100 microns when the metal sulphides are of a size of the same magnitude.

Then unit processes are applied, such as, for example gravity separation, magnetic separation, flotation or another process, where the particles are separated in two fractions, one with higher metal content, which is known as concentrate in the mining lexicon, and a second fraction with low metal content, which is known as tails. Bio-oxidation processes may also be applied to the solubilization of the metal sulphides in concentrates or tails.

Hereinafter, the term "ore" refers to any material which contains a metal compound or sulphur as a microbial substrate. As an example, but without limiting the scope of the invention, the term ore includes minerals, concentrates, tails, coals, etc.

It is known that microbial species oxidize insoluble sulphide minerals into soluble sulphates, either directly or indirectly. In the case of direct oxidation, the destruction of the crystalline structure of the sulphide mineral takes place by the enzymatic systems of the acting microorganisms. The indirect oxidation of sulphide minerals is due to the action of the ferric ion ($Fe^{3+}$), which, in turn, is a product of the bacterial oxidation of ferrous iron and iron-containing sulphide minerals.

The chemistry of pyrite biological oxidation via the most probable reaction is as follows:

$$4FeS_2 + 15O_2 + 2H_2O \rightarrow Bacteria \rightarrow 2Fe_2(SO_4)_3 + 2H_2SO_4$$

The above reaction illustrates the direct bacterial oxidation of pyrite. The resulting ferric sulphate, in turn, oxidizes pyrite, forming ferrous sulphate and elemental sulphur:

$$FeS_2 + 7Fe_2(SO_4)_3 + 8H_2O \rightarrow Chemically \rightarrow 15FeSO_4 + 8H_2SO_4$$

$$FeS_2 + Fe_2(SO_4)_3 \rightarrow Chemically \rightarrow 3FeSO_4 + 2S°$$

Ferrous iron and sulphur undergo bacterial oxidation:

$$4FeSO_4 + O_2 + 2H_2SO_4 \rightarrow Bacteria \rightarrow 2Fe_2(SO_4)_3 + 2H_2O$$

$$2S° + 3O_2 + 2H_2O \rightarrow Bacteria \rightarrow 2H_2SO_4$$

In the case of chalcocite ($Cu_2S$), cuprous ion ($Cu^{1+}$) and sulphide ($S^{2-}$) are oxidized by the microbial enzymatic systems to $Cu^{2+}$, $S°$ and $SO_4^=$.

By similar mechanisms, the bacterial oxidation of a wide spectrum of sulphide minerals is possible. Thiobacillus ferrooxidans and related bacteria oxidize the uranous ion according to the following reaction:

$$2U^{4+} + O_2 + 2H_2O \rightarrow Bacteria \rightarrow 2UO_2^{2+} + 4H^+$$

The leading role in uranium leaching is played by ferric iron. $Fe^{3+}$ oxidizes $U^{4+}$ to $U^+$ which is solubilized in sulfuric acid solutions.

$$UO_2 + Fe_2(SO_4)_3 \rightarrow Chemically \rightarrow UO_2SO_4 + 2FeSO_4$$

$$UO_3 + H_2SO_4 \rightarrow Chemically \rightarrow UO_2SO_4 + H_2O$$

The bacteria regenerate $Fe^{3+}$ by oxidation of $Fe^{2+}$ or $FeS_2$.

By reactions similar to the above, a wide variety of mineral compounds can be oxidized. The most important microorganisms in biohydrometallurgy are presented in Table I.

TABLE I

Important Microorganisms in Biometallurgy

| Microorganisms | Process | Feasible area of application |
| --- | --- | --- |
| Bacteria of the genus Thiobacillus and Leptospirillum: *Thiobacillus ferrooxidans* *Thiobacillus thiooxidans* *Thiobacillus acidophilus* (Syn. *T. organoparus*) *Leptospirillum ferrooxidans* in mixed culture with *T. thiooxidans* and *T. acidophilus* | Oxidation of sulphide minerals, S° and $Fe^{2+}$ at pH = 1.4–3.5 and T = 5–35° C. | Dump, underground and tank leaching of metals from sulphides, mixed ores and concentrates, from wastes of pyrometallurgic industry. Desulfurization of coals. Precious metal's purification. |
| Facultative Thermophilic bacteria similar to thiobacilli | Same at pH = 1.1–3.5 and T = 30–55° C. | Same as above |
| Facultative Thermophilic bacteria of the genus Sulfobacillus | Same at pH = 1.1–3.5 and T = 20–60° C. | Same as above |
| Acidophilic bacteria of the genus sulpholobus and Acidianus | Same at pH = 1.0–5.0 and T = 45–96° C. | Same as above |

As indicated in Table I, the main areas of application of the biohydrometallurgy processes are: metals leaching, coal desulphurization and precious metals purification. These areas will be briefly discussed herein below:

Leaching of Metals

At present, the microbial leaching of metals takes place by different processes that depend on the scale and characteristics of the mineral involved.

In-situ microbial leaching may be considered as a specialized underground extraction system involving the microbiologically enhanced dissolution of metal elements from run-of-mine ores with grades ranging from above the cut-off grade to the so-called submarginal or submilling grades. Leach solutions are injected into, and percolate through the rock mass. When the dissolution of the desired metal values is achieved, the solutions are collected and pumped to the metal recovery plant.

Microbial dump leaching may be defined as a "metal scavenging" method employed for recovering metal elements from lean ores, (i.e., that part of the ore body containing rock with grade below the cut-off and which must be removed in order to enable access to the richer parts of the mineralization). These rocks are accumulated in dumps located in the vicinity of the open-pit. The top of the dump is irrigated with leach solutions containing microorganisms. These solutions percolate through the broken rock mass, solubilizing the metal elements. The pregnant solutions flow out of the bottom of the dump and are finally collected in ponds and then pumped to the metal recovery plants.

Microbial heap leaching is a method in which the crushed ore is piled up in regular layers on appropriately prepared areas. The heap is a truncated pyramid. The controlling dimension of size is the height of the heap which is related with the gradation of the mineral. The top part of the heap is irrigated with leach solutions containing microorganisms and percolate continuously through the mineral.

Microbial tank leaching is a process whereby metals are leached from ores and concentrates in Pachuca tanks, reactors or conditioning tanks. The pulp formed by the mineral and the leach solution, once inoculated, is stirred and aerated in a temperature regulated system.

In the biotechnological practice, the dilution of the pulp expressed as the liquid to solid rate mass contained in a given mass of pulp, ranges from 4 to 10.

It should be pointed out that even though the different leaching processes developed and put into practice so far have distinctive characteristics, all have a common feature: the ores or concentrates are suspended, flooded, and/or subjected to percolation with aqueous solutions in such a way that the microorganisms are confined to an aqueous environment.

Coal Desulphurization

Coal contains elemental sulphur in variable quantities and mainly in pyrite form ($FeS_2$). The combustion of coal results in the conversion of the existing sulphur to $SO_2$, which pollutes the atmosphere causing acid rains with the consequent damages to vegetation, animals and human health. In order to keep appropriate levels of sulphur dioxide in the atmosphere in areas where coal is burned in great scale, low-sulphur coals should be exploited, generally with a total sulphur content below 1 to 1.5%.

Isolation of *T. ferrooxidans* from acid drainages of coal mines has generated interest due to its potential to desulphurize coal by oxidation of sulphur and pyritic minerals.

Microbial leaching of sulphur compounds from coal has been practiced along similar guidelines and under the criteria developed for microbial leaching of metals, that is, the microorganisms must act in an aqueous environment.

Several microorganisms have proved to be effective in coal desulphurization according to conventional techniques. However, the process cannot be practiced at industrial scale under such conditions, essentially due to the long processing time and high processing volumes required as a consequence of the low microbial activity.

Precious Metals Purification by the Liberation of Sulphide Minerals

It has been demonstrated that when concentrates containing pyrite, arsenopyrite and finely dispersed gold, are subjected to bioleaching prior to cyanidation, most of the sulphide minerals are dissolved and the gold yield is substantially increased by subsequent cyanidation.

Considerations About the Optimization of Biometallurgical Technology

Biometallurgy has generated worldwide interest because of its potential advantages over the conventional extractive metallurgical processes. These advantages are as follows:

Low energy consumption

Low chemical reagents consumption

Low investment cost

It is a clean process which does not pollute the environment.

It allows for the economical exploitation of low grade deposits.

However, in the present state of development, the application of this technology requires long processing times, from several months to years in order to obtain acceptable recoveries. The leaching velocity is low, and this is attributable to the low multiplication velocity of the responsible bacteria.

The processing time constitutes, by itself, a significant technical-economical barrier for the purposes of industrial application. Also, the low leaching velocity requires operating with large masses of mineral that, in general, are subject to climatic variations, preventing the precise control of the systems which become fluctuating and erratic and result in variable and unpredictable processing times.

The study of physiological characteristics, conditions of growth and development of microorganisms related to oxidation of metallic compounds, applied to the solution of the above-mentioned technological problems, constitutes an important area of investigation encompassing the principles on which the present invention is based.

State of the Art

Bacterial leaching can be used at present to recover, on a commercial basis, metals from minerals. This is done through the percolation of acid solutions on heaps, dumps or in situ in mine deposits, and collecting the solution containing the metals for further purification. However, these processes are much slower than other commercial leaching processes, such as vat leaching with bacteria. One of the most important microorganism involved in the above processes is *Thiobacillus ferrooxidans*.

The usual process to recover metals using this technology consists in the pumping of acidic solutions, usually at pH about 2, containing ferrous ions, about one gram per liter, to the top of a dump or heap, containing the mineral with the metal sulphides. The bacteria are normally indigenous to such dumps and should grow and multiply as the leaching proceeds. The same is true in underground or in situ leaching, where the solution is recirculated through part of the mine. (See SME Mineral Processing Handbook, edited by Norman L. Weiss, published by Society of Mining Engineers of the American Institute of Mining, Metallurgical, and Petroleum Engineers, Inc., New York, 1985).

The known methods to oxidate sulphide minerals are based on the acidification of the mineral, sometimes crushed to sizes of 1 inch or less, which is done by irrigation with sulphuric acid solutions. The solution is spread by irrigators. Sometimes the acid is added to the crushed mineral, at moistures beyond supersaturation. This ore is stacked in heaps or dumps, on an impervious layer that can be plastic or compacted soil with clay. The solution is irrigated on the top, and drains throughout the mineral, being collected on the impervious layer or membrane, and this solution contains some of the metals dissolved.

To achieve good metal dissolution using these methods for metal sulphide minerals, the required time varies from several months to many years. As an example, it takes 4 to 5 years in heaps irrigated with sulphuric acid solutions to achieve 75% recovery of copper from a mineral containing copper sulphide minerals.

Before the present invention, the bio-oxidation of metal sulphides was performed at high liquid to solid ratios, producing bio-oxidized products as solutions, with two phases clearly present. In the method of the present invention, one performs the bio-oxidation of metal sulphides, and the products of the reaction are crystal-like solids, such bio-oxidation solid products being microbial colonies.

Killgore, in U.S. Pat. No. 3,883,310, describes a vessel which allows one to control the conditions for a liquid system which has common features to all known leaching systems. The microorganisms are suspended in a leaching solution and take dissolved oxygen from the solution. The present invention is quite different. In the present invention, the microorganisms are confined to grow attached to the ore taking the oxygen directly from the air and produce the bio-oxidized compounds in solid state.

In the mining lexicon, the words "dry, drying period, dry cycles, or irrigation and dry" are quite standard and mean that there is no irrigation being applied, which does not necessarily mean that the moisture is close to zero. During the "dry" periods in the mining industry, the heaps or dumps or the parts of a mine subjected to leaching, continue producing drainages, that is to say, these operations are with over supersaturated moisture, even when the lexicon qualifies these operations as dry. For example, P. T. Malakhova and S. I. Mukhamedova, found that the alternate irrigating and drying of the ore improved the leaching efficiency in the case of copper ores. The above procedure is usual in the mining industry where periods of irrigation are followed by periods of drainages. These periods were two, three or six month drying periods; however, a suitable or effective loss of water was not allowed for in these periods. In the so called long drying periods, only the surface layer of ore on the heap is dried out.

In the above-mentioned conditions, the water film covering the ore particles has a sufficient thickness for confining the microorganisms, with one micron size, to develop in a liquid film. The annual copper recovery obtained by Malakhova was 9.4% of the copper. Using the present invention, recoveries much higher than that may be obtained in hours or days.

Actual conditions for tank leaching of ores and concentrates may be illustrated by U.S. Pat. No. 4,571,387, in which bioleaching is carried out by contacting the ore or concentrate with an aqueous acid leaching medium containing sulphide oxidizing bacteria, the liquid to solid ratio being approximately 4.5/1. The bio-oxidized products are obtained, dissolved in the liquid phase and when the bioleaching process is completed the two phases, liquid and solid, must be separated.

A process for refractory sulphide concentrates obtained by bioleaching is disclosed in a paper by R. W. Lawrence and A. Bruynestein entitled "Biological Pre-oxidation to enhance Gold and Silver Recovery from Refractory Pyritic Ores and Concentrates" (CIM Bulletin, September 1983, pp. 107–110).

U.S. Pat. No. 4,729,788 illustrates the recovery of precious metals from refractory sulphide ores, concentrates, tailings, among other sulphide materials. The method disclosed therein comprises bio-leaching a mineral sulphide containing occluded precious metals with an aqueous solution. The pulp density is between 5 to 15% solids. When bio-leaching is completed, two phases, a solid and a liquid, must be separated by a solid-liquid separation method. The solid phase is treated with specific leaching agents to recover precious metals. The liquid phase contains the microorganisms. It must also be noted that the oxidized products are obtained in the liquid phase in the form of solutions.

Microbial desulphurization of coal has been carried out in slurries constituted by two phases: a solid and a liquid phase. The microorganisms develop suspended in the liquid phase and the soluble sulphur compounds are produced dissolved in the liquid phase. A solid and a liquid phase must be separated after completion of the biooxidation process. These methods are discussed in U.S. Pat. Nos. 4,456,688, 2,829,964, 3,796,308, and 4,861,723.

All the above processes, which illustrate the known state of the art, are entirely different from the present invention where the acidification may be performed with the minimum volume of acid solution that ensures the total and homogeneous acidification of the substrate, allowing evaporation after that. Stated another way, during and after the biooxidation step, the system has only one phase, that is a solid phase, and the bio-oxidized products are obtained in solid state, such solid products being microbial colonies. These conditions allow high recoveries in hours or days due to the high bacterial multiplication velocity. These features manifest the novelty, non-obviousness and utility of the present invention and clearly distinguish the present invention from any other known methods.

SUMMARY OF THE INVENTION

The present invention relates to a biometallurgical process in which mineral compounds contained in ores and constituting substrates for microorganisms are bio-oxidized to allow solubilization and separation thereof. More particularly, the present invention relates to a process that considerably increases the microbial oxidation velocity of mineral compounds. The essential principle of this process is based on the discovery of the behavior of bioleaching bacteria with respect to water.

The present invention is applicable to a wide range of microorganisms, of different strains, as is shown in TABLE II and throughout the examples. Thus, this invention does not depend on the use a particular microorganism. The invention enables the microorganism in question to develop in a new and faster way.

Strains of any of the genera indicated in TABLE I and TABLE II are applicable to the present invention, and they may be obtained from public collections such as the ATCC (American Type Culture Collection).

Alternatively, general methods for obtaining such microorganisms have been explained in the literature and are universally used in order to obtain useful microorganisms from natural sources such as from mine drainage.

As noted above, a general procedure for obtaining a source of strains from natural environments is described in the literature, and a summary of this method, without limiting the scope of this invention, is to utilize the following recommended steps:

1. Select a mine of a metal sulphide.
2. Select an acid drainage of the mine.
3. Take a sample of the drainage, including a liquid and a solid portion. (e.g., 50 to 500 grams)
4. Add this sample to a bottle with 9K Medium, obtained from any chemical reagent supplier (24,000 ppm of $FeSO_4$, 820 ppm of $NH_4+$, 235 ppm of $PO_4(3+)$, and 95 ppm of $Mg(+2)$, with traces of other elements that are essential nutrients, such as Calcium and Potassium if these are not in the acid drainage). Take, as an example, one liter of the mentioned 9K Medium.
5. Maintain the above mixture in a controlled temperature incubator, for example, at 28 centigrade for three weeks with the bottle open but stoppered with a cotton swab.
6. Changes in color from brown to reddish reveals the presence of the oxidating strains. Take a sample of the solution and transfer to another bottle with 9K Medium.
7. Use the above mixture as a source of strains.

For isolating pure cultures of any of the microbial genera indicated in TABLE I, the following literature references may be useful:

Harrison, Jr. A. P., (1984) *Ann. Rev. Microbiol.* 88: 265–292.

Vishniac, W. V., Santer, M., (1957) *Bacteriol. Rev.* 21: 195–213.

Manning, H. L., (1975) *Appl. Microbiol.* 30: 1010–1016.

Brierley, J. A., Lockwood, S. J., (1977) *FEMS Microbiol. Lett.* 2: 163–165.

Karavaiko, G. I., (1988) *Biogeotechnology of Metals Manual.* Scientific Editors: Karavaiko, G. I. (U.R.S.S.), Rossi, G. (Italy), Agate, A. D. (India), Grouder, S. N. (Bulgaria), Avakyan, Z. A. (U.R.S.S.). Centre of International Projects GKNT. 47–86.

Touvinen, O. H., Kelly, D. P. (1973) *Arch. Mikrobiol.* 88: 285–298.

Schrader, J. A., Holmes, D. S. (1988) *J. Bacteriol.* 170 :3915–3923.

Ahonen, L., Touvinen, O. H. (1991) *Appl. Environ. Microbiol.* 57: 138–145.

Norris, P. R., Marsh, R. M., Lindstromom, E. B. (1986) *Biotechnol. and Appl. Biochem.* 8:318–329.

Another manner in which to obtain useful microorganisms, without excluding the other methods, nor limiting the scope of this invention, consists of the following steps:

1. To select a metal sulphide of interest for bio-oxidation, and to select the temperature of bio-oxidation.
2. To select an ore containing such metal sulphide.
3. To put a weighed quantity of such ore, for example 10 to 15 grams, into plates.
4. To add to each plate different volumes of a sulphuric acid solution in such a way as to obtain in each one a different initial ratio liquid to solid, for example 0.2 to 1.0.
5. To repeat step 4 for different sulphuric acid concentrations, for example from 0.2N to 2N.
6. To incubate all the prepared plates according with steps 4 and 5, opened, at a selected temperature according to the strain which one expects to isolate.
7. When the plates are dry in aspect, that is, there is a change in color revealing that there is not any longer supersaturated moisture, analyzing visually all of them to detect which one presents crystal-like solids, which color is according to the corresponding metal sulphate of the metal sulphide selected in step 1.
8. To isolate one of the above mentioned crystal-like solids in step 7, and to dissolve these crystal-like solids in a few drops of 0.06N sulphuric acid solution. To determine by microscopy the presence of microorganisms coming from the solid. Sometimes the microorganisms are better observed if the crystal-like solid is suspended in 1% sarkosyl solution.
9. If the steps 7 and 8 do not give the described results, a second microbial enrichment may be necessary. This second microbial enrichment is carried out by repeating steps 4 to 7 in the same plates after step 7.
10. For isolating pure cultures, plates must be prepared containing for example, 1 or 2 grams of the metal sulphide in question. Sulphuric acid solutions of different concentrations, for example 0.2N to 5N, are added to each plate. For each acid concentration, different initial liquid to solid ratios, for example, 0.25 to 2.0 are added.

11. 10 milliliters of 0.06N sulphuric acid solution are then added to a plate where a microbial enrichment has been reached according to steps 3 to 8. To dissolve the solid bio-oxidized products and to suspend the microorganisms by rotating the plate.

12. The plates prepared according to step 10 are then inoculated with 100 microliters of the suspension resulting from step 11.

13. All the prepared plates according with steps 10 to 12 are then incubated at the selected temperature.

14. From the plates having solid bio-oxidized products which look like crystals, these being microbial colonies, one isolates one colony with a sterile spatula.

15. By subculturing this colony two or three times in the same conditions as it was obtained, by using sterile materials, a pure strain will be obtained.

The above-described method for obtaining microorganisms that can be used in the present invention gives the best conditions of acid concentration, initial liquid to solid ratio for a certain microorganism, and a certain temperature for a certain ore. The described procedure will be referred to hereinafter as the "before-hand predetermined conditions". Variations of these conditions can be allowed to occur for purposes of the present invention.

Industrially, it is a common practice in the known systems of bioleaching of metals, as dumps or heaps, to utilize the ore's own microflora, which enrichment is produced as the system is developed. This system does not work with pure strains, but with a mixture of strains.

In the present invention, it is possible to use enrichment of the ore's own microflora.

For this, the ore must be pelletized with an acid solution which concentration may be for example, between 3 and 5N and at a liquid to solid ratio, for example, between 1/15 and 1/25. The ore so prepared is placed in trays or in columns, and the natural or artificially induced dehydration is allowed until bio-oxidation occurs giving solid products looking like crystals which are microbial colonies.

A second and a third microbial enrichment may be carried out by repeating the pelletization at the same conditions under which the enrichment was obtained in the first stage and allowing for the subsequent dehydration. This method is a manner of applying the invention by using the ore's own microflora. Furthermore, ore portions coming from any of the microbial enrichment stages, may be used as inoculums for subsequent bio-oxidation processes.

The previous method indicates a manner for applying the invention by the enrichment of the ores's own microflora.

BRIEF DESCRIPTION OF THE FIGURES

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
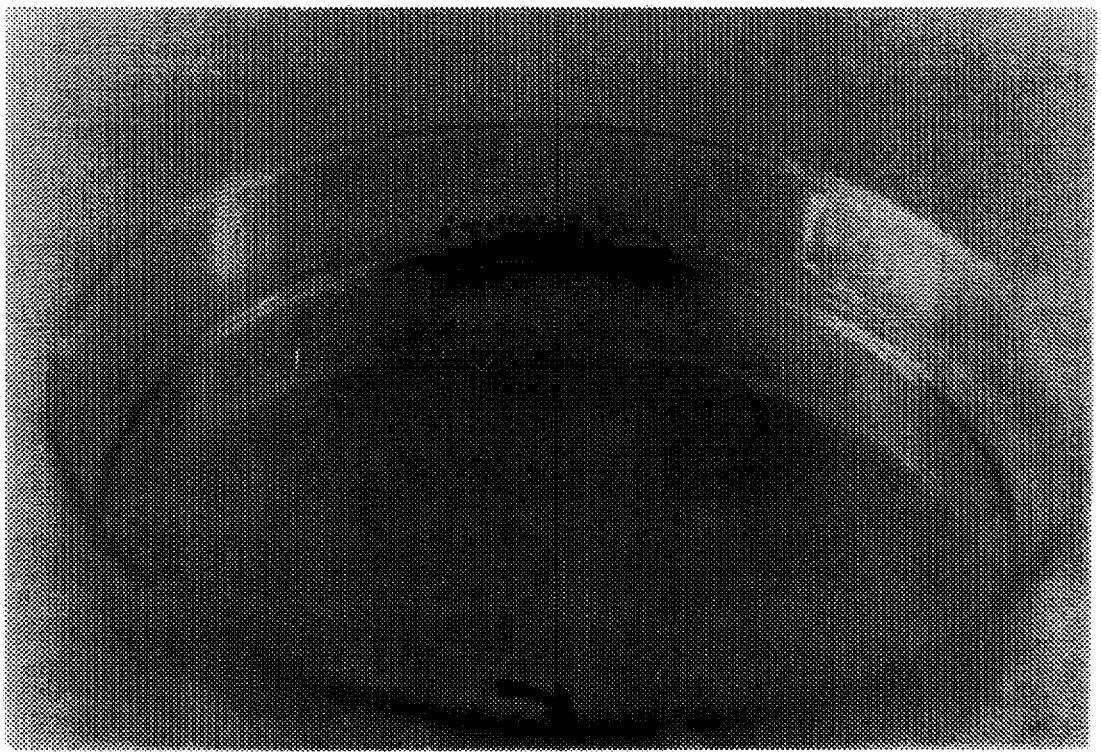
FIG. 1 shows colonies on the dehydrated, thinnest edge of a plate with an agarized ferrous medium. The arrow indicates the inoculation place.
Figure 2:
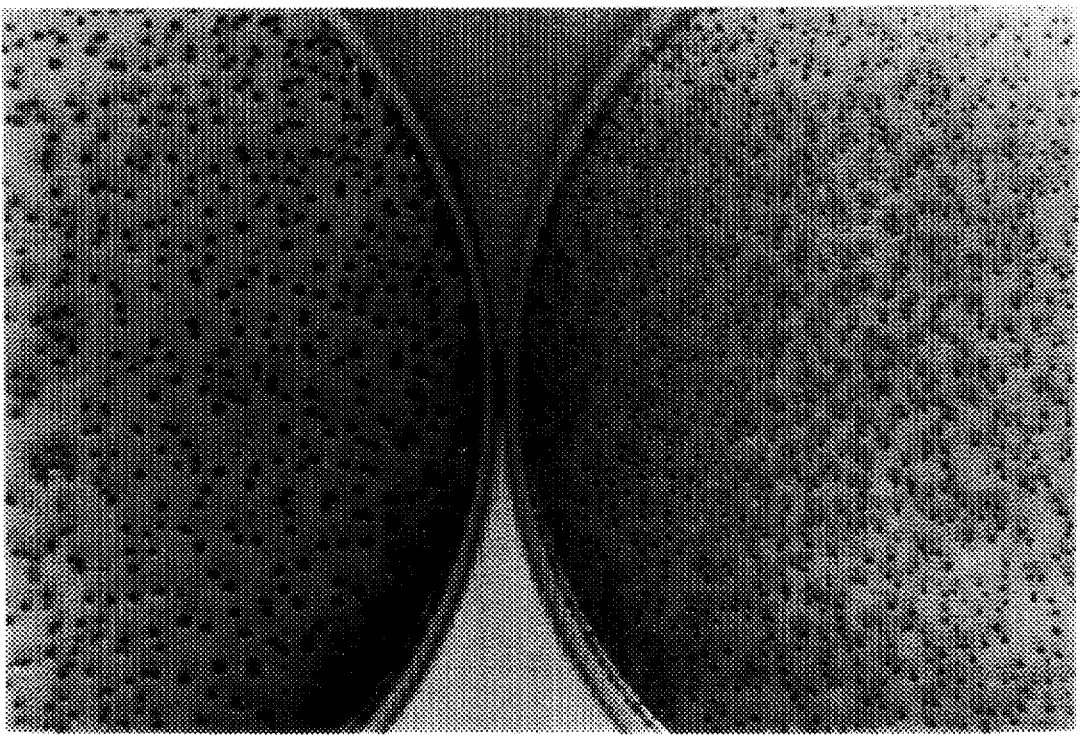
FIGS. 2, 3, 4 and 6 shows colonies obtained from dehydrated agarized ferrous media.
Figure 3:
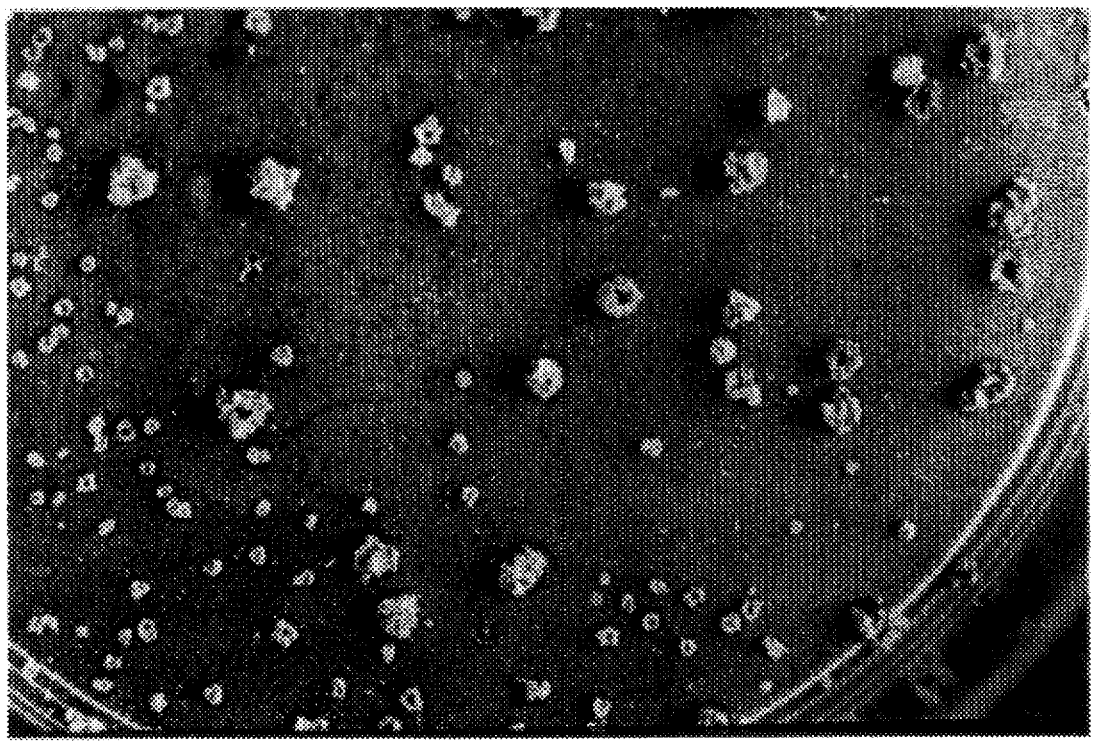
Figure 4:
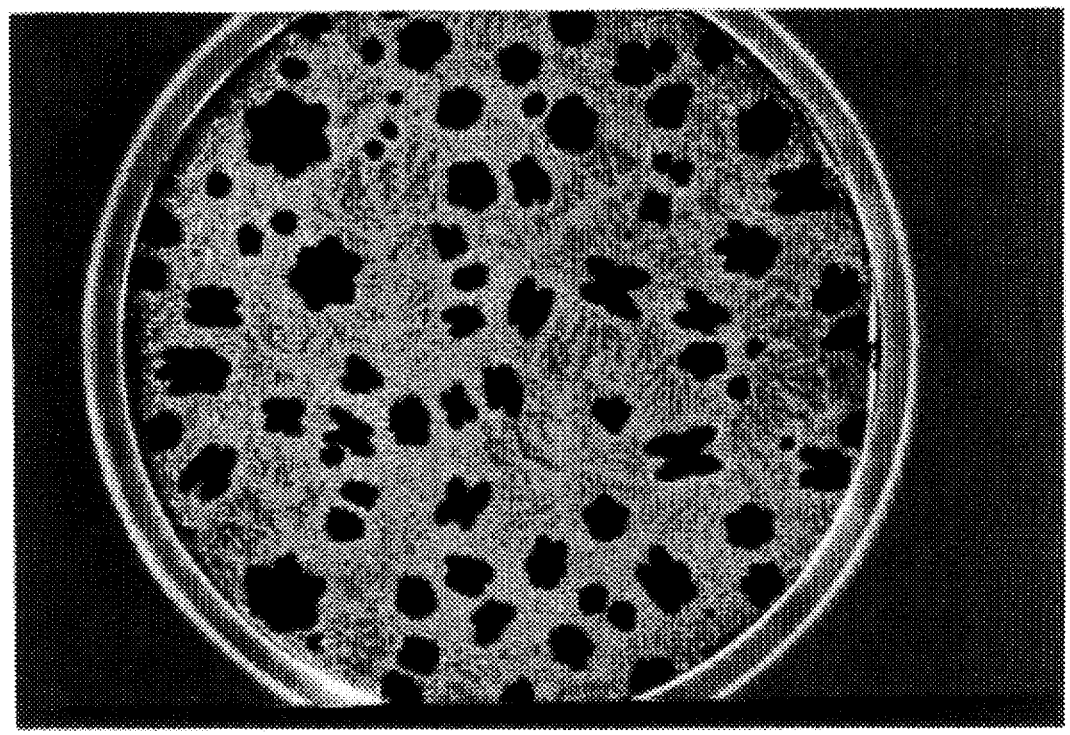

In the present invention, insoluble mineral compounds such as metal sulphides, sulphur, metal oxides, or ferrous compounds, said compounds being contained in ores and said compounds being substrates for microorganisms, are bio-oxidized to convert said insoluble compounds into soluble sulphates or oxides to allow separation thereof.

The process of the present invention comprises the steps of:

a) Conditioning the ore with an acidic solution;

b) Adding a microbial inoculum to said conditioned ore;

c) Drying said conditioned and inoculated ore until soluble bio-oxidized products in solid state are obtained as microbial colonies;

d) Maintaining said ore at a selected range of temperatures according to the growth requirement of the microorganisms, until bio-oxidation is completed; and e) Separating out the soluble solid products in solid state obtained as a result of said bio-oxidation by said microorganisms.

Utilizing more detail, the process of invention is characterized by the following steps:

a) Conditioning the ore with the quantity of acid which is determined before-hand as the most convenient in order to: 1) neutralize the ore, 2) prevent compaction, 3) and provide the proper acidity for the microorganisms.

The quantity of acid used is preferably contained in the smallest possible volume of a solution. Alternatively, one may contact the ore with acid vapors so as to homogeneously acidify the substrate while introducing the smallest possible amount of water into the system.

The other steps of the process are as follows:

b) Adding a microbial inoculum capable of oxidating the mineral compound of interest, or enriching the mineral ore's own microbial flora. The addition of a microbial inoculum may be carried out either simultaneously with or independently from step a);

c) Enabling the spontaneous or induced loss of the excess water that may be present in the conditioned ore by natural evaporation or by drying with flowing air until the thermodynamically available water is sufficiently low enough to obtain the bio-oxidation products in solid state, said bio-oxidation products, in turn, constituting microbial colonies;

d) Maintaining said ore at a selected range of temperatures according to the growth requirement of the employed microorganisms. For the best results, the ore, at least during the bio-oxidation, must be at a temperature within the optimum temperature range of the microbial species employed; and e) Separating the bio-oxidation products.

The metals may be separated by washing with water, by washing with acidic or other aqueous solutions, by screening, by gravity separation, or by flotation.

Small quantities of chemical elements, for example, potassium, phosphorus, magnesium, calcium and nitrogen, are essential for bacterial growth. Generally, the ore's contents or even the impurities in the concentrates are sufficient for bacterial growth. Nevertheless, the requirement of adding some or all of the above-chemical elements must be analyzed for each particular ore.

Consequently, the process described above may further comprise the step of adding an inorganic chemical compound to step (a). The inorganic chemical compound may be present in the form of a salt or an aqueous solution and said salt or aqueous solution comprises at least one element selected from the group consisting of potassium, phosphorus, magnesium, calcium and nitrogen.

The acidic solution of step (a) may be reduced in volume by adding to said solution an agent selected from the group consisting of wetting agents, tensoactive agents, detergents and surfactants.

The reduction in the acidic solution volume positively affects the process since the system has a lower quantity of water. Thus, the requirements of drying are lower.

The smallest amount of the acidic solution for reaching an homogeneous acidification for each ore has a limit. By using wetting agents, tensoactive agents, detergents or surfactants, the acidic solution volume required for getting a homogeneous acidification is smaller than the smallest volume required without these agents.

The water activity may be decreased by addition of a dehydrating agent selecting from the group consisting of:

polyols, glycols, esters of glycols, ethers of glycols, polyglycols, polyglycol esters, polyglycol ethers, heavy metal sulphates, calcium salts, magnesium salts, silicic acid, sodium silicate, sulphuric anhydride, or a mixture thereof.

Dehydrating agents are used for decreasing the water activity in order to get a quick bio-oxidation velocity. In this manner, the requirements of drying may be reduced or eliminated according to the type and quantity of the employed dehydrating agent.

To illustrate the above-concept, a quick bio-oxidation without the requirements of drying are obtained in concentrates by using between 30 and 160 kilograms of $CaCl_2$ per ton of concentrate. Using these conditions, the reaction is immediate and does not require drying.

Quick bio-oxidation by adding dehydrating agents to decrease the water activity may also be applied for other ores, thereby decreasing or eliminating the drying requirements. Nevertheless, in each case, the economy of the process must be considered in connection with the cost and quantity of the employed dehydrating agent, as well as the economic value of the ore in question. Dehydrating agents may be used for bio-oxidation of tails, but it could be costly, but they are very attractive for use with concentrates.

With respect to mineral, between 5 and 15 kilograms of $CaCl_2$ per ton of a copper mineral notably reduce the requirements in drying, giving better extraction yields, when compared with the same assays without the use of a dehydrating agent.

The previous concept relating to the use of dehydrating agents cannot be entirely separated from reducing the volume of the acidic solution. They are different ways to achieve the same objective: to establish the lowest thermodynamically available water or water activity in the system.

As noted above, the quantity of acid for conditioning the ore is determined before-hand as the most convenient, in order to neutralize the ore to prevent compaction and to provide the proper acidity for the microorganisms.

The quantity of acid used is preferably contained in the smallest possible volume of a solution, in such a way as to acidify homogeneously the ore introducing into the system the smallest quantity of water.

It should also be noted that, rather than providing a microbial inoculum, one may enrich the mineral ore's own microbial flora, as noted previously. This is accomplished by homogeneous acidification of the ore with a sulphuric acid solution. The most convenient volume and concentration must be determined before-hand as was indicated previously. The best conditions of acidification depend on the physical and chemical characteristics of the ore in question.

As noted above, the system must be dried. Natural or induced drying is allowed until the thermodynamically available water is sufficiently low enough so that the microorganisms are not suspended in a liquid film. Thus, one allows for the spontaneous or induced water excess that may be present in the system by evaporation or by drying with flowing air until the thermodynamically available water is sufficiently low enough for obtaining the bio-oxidation products in solid state. At this point, each microbial cell attached to a sulphide compound can bio-oxidate the compound giving a solid soluble product looking like a crystal and containing in the solid product thousands or millions of cells coming at least theoretically from one cell. In this manner, the ore is numerically enriched by its own microbial microflora. The bio-oxidation products constitute microbial colonies.

In a second cycle, the ore must be homogeneously humidified another time with the same criteria applied in the first cycle. In this way, the soluble solid products produced in the previous cycle are, at least partially solubilized, liberating the contained microbial cells, which can come into contact with other insoluble compounds not bio-oxidized in the first cycle. By subsequent natural or induced drying, they will be bio-oxidized.

The prior processes may be repeated until one reaches a commercial yield of bio-oxidation for subsequent extraction. When a microbial inoculum is used, the microorganisms may be added during or subsequent to the addition of the conditioning acidic solution.

The drying of the system is one way for getting the microorganisms not to be suspended in a water film, and for allowing for a stable attachment of the microorganisms to the insoluble sulphide or oxide compounds which are their substrates. A high bacterial multiplication velocity associated with a high bio-oxidation velocity is obtained.

The air contact is very important for the bio-oxidation process, taking into account that the bacterial growth requires carbon dioxide, nitrogen and oxygen from the air.

The concentrates are generally in the form of thin powders. One way for getting a high specific surface area of a conditioned and inoculated concentrate in contact with air is by pelletizing said conditioned and inoculated concentrate with a coarse inert material such as: triturated rocks, gravel, glass balls, plastic balls, rubber balls, etc. A layer of the conditioned concentrate surrounds the inert pelletization material allowing for a high specific surface area in contact with air.

Good results have been obtained also by distributing the conditioned and inoculated concentrate as layers on both sides of an inert material sheet.

The prior criteria may be applied for other ores when they are of sugar grain-sized or smaller. In this manner, it is possible to get a higher contact between the substrates and air.

Generally, the metal sulphides or oxides or sulphur are found in nature as particles disseminated in rocks, the association of both being considered as an ore. For reaching a high conversion, by bio-oxidation of those particles giving soluble compounds, it is necessary that at least one microbial cell comes into contact with each particle, getting a stable attachment and a high multiplication velocity associated with a high bio-oxidation velocity of those particles which have got at least the attachment of one cell after drying.

The insoluble compounds which, at the point of adequate dehydration do not have at least one cell attached, will not be oxidized. So, it is possible even using the addition of an inoculum, not to get a commercial bio-oxidation yield. It depends on the number of cells in the inoculum and the dissemination degree of the insoluble substrates. In this case, equivalent procedures as those indicated for the ore's own microflora enrichment may be carried out.

The water content may be increased and decreased alternatively through a number of cycles. The water content increase is allowed according to step a) to release the microorganisms contained in the bio-oxidized solid products obtained through the step of drying in the first cycle. After that, the water content is decreased by drying in the same form as it was in the first cycle in order to obtain the bio-oxidation of the particles not bio-oxidized in the previous cycle.

A number of cycles, including humidification and drying, may be carried out in order to get a commercial bio-oxidation yield.

Different microbial species have different ranges of temperatures for optimal growth and high activity, as is shown in Table I (Process) for microbial species important in Biometallurgy.

Below, in Table II, by way of example, strains corresponding to different species are indicated and have been employed in the present invention. The strains have been characterized, among other features, according to the optimum temperature range. Microorganisms having different temperature range of growth, may be employed in the present invention.

For the best results, the ore, at least during the bio-oxidation steps, must be at a temperature within the optimum temperature range of the microbial species employed.

As noted above, in all the known biohydrometallurgical systems, bio-oxidation is carried out with the microorganisms suspended in a liquid phase. Thus, the known systems have two phases: a solid phase, constituted by the ore, and a liquid phase constituted by the leaching solution, where the microorganisms are suspended. The bio-oxidized products are obtained as solutions, that is, they are produced solubilized in the liquid phase. Thus, during the bio-oxidation step and when the bio-oxidation finishes, the system has two phases, a liquid and a solid phase, which may be separated.

Even in known systems, where words such as dry, drying period, dry cycles or irrigation and dry are used, meaning that there is no irrigation being applied during such periods, heaps or dumps, or the parts of a mine subjected to leaching continue producing drainages. This is to say, the operations are over-supersaturated moisture and the system during the bio-oxidation step has two phases: a liquid and a solid phase. Both phases may be separated giving the bio-oxidized products solubilized in the leaching solution, that is in the liquid phase.

By the present invention, the bio-oxidation is carried out when the system has a moisture below the supersaturated state. The supersaturated state occurs when additional water cannot find room without generating a pore pressure that once again forces the particles apart, causing them gradually to lose contact with one another.

By the process of the invention, during the bio-oxidation and when the bio-oxidation finishes, it is not possible to separate a liquid and a solid phase. It is also not possible to have drainage during the bio-oxidation step or when bio-oxidation finishes. The system has only one phase, that is, a solid phase and the soluble bio-oxidized products are in solid state, being microbial colonies.

By the process of the invention, the soluble bio-oxidized compounds are obtained in solid state during the bio-oxidation step. For separating them from the remainder of the material, the bio-oxidation step must be followed by a separation step.

The separation step may be carried out by suitable methods such as: washing with water, washing with aqueous solution, screening, gravity separation, or flotation.

When separating by washing, the soluble bio-oxidized compounds in solid state, obtained during the bio-oxidation step, are solubilized in the washing solution and must be separated in this step by separating the washing solution from the remaining solid material.

When the invention is applied to metal extraction, the soluble bio-oxidized compounds are the products of interest in the process. They are separated in the separation step, and the remaining material constitutes the residue or tail.

When the invention is applied to purification processes, such as coal desulphurization or precious metal purification, the soluble bio-oxidized compounds separated by the separation step constitute the residue while the remaining material constitutes the product of interest.

The first stage of interaction of bioleaching microorganisms with a solid inorganic substrate consists in their attachment to the surface, whereupon the substrate being oxidized is attacked biochemically. Attachment is specific to the mineral compounds which offer a source of energy, but such attachment is not frequent and does not always occur in the systems tried so far. The conditions which allow or facilitate a stable and efficient attachment, enabling the bacteria to transform the substrate and multiply quickly, had not heretofore been explained.

From the physiological characterization and development conditions hereinafter described, it is clear that these microorganisms have a definite hydrophobic character. In other words, the water, or at least the water levels in conventional systems, make the stable attachment of cells to the substrates difficult.

The phenomena that take place when the cells and the surface of mineral compounds interact or the mechanism of destruction of the sulphide mineral lattice are not clear. Although there are different theories, it is generally believed that enzymatic mechanisms are involved in this interaction. In such case, the intervening enzymes must not be diluted or washed out from the reacting surface.

One important aspect of the present invention is the micro-environment in which the microorganisms are confined to develop. If a rock one inch in size has a liquid to solid ratio of 1:10, that is, 10% moisture, each ore piece is surrounded by a liquid film of sufficient thickness for confining the microorganisms, one micron in size, to live and to develop suspended in a liquid medium with a low multiplication and bio-oxidation velocity.

If a finely ground ore is agglomerated with an acid solution, it is possible to obtain quick growth and to obtain formation of products in solid state when the liquid to solid ratio is 1:10 and sometimes higher, depending on the specific area and the chemical composition of the ore.

The higher the ore specific area, the thinner the water film for a fixed liquid to solid ratio. The water film must be thin enough to ensure the proper microbial attachment to the substrate surfaces and to allow the microorganisms to multiply quickly giving the soluble bio-oxidized products in solid state.

A second consideration is the pattern of the solution layer which is the boundary between the solid surface and the solution. The thickness of that layer, which performs as a solid, is a function of the chemistry of the solution. There are ions which permit a thick layer of water to perform as a solid.

A third consideration is the water activity which is a measurement of the available free water next to the solid surfaces, and depends on the water present and on the electrolytes present which are different for different ores. Furthermore, the water activity may be artificially reduced, as shown in the present invention, by the addition of chemical compounds known as dehydrating agents as polyethyleneglycols, inorganic salts or any chemical compound with the ability to decrease the water activity.

From the above considerations, it is clear that the range of moisture contents present at the time of developing the microorganisms in a faster way, yielding bio-oxidized products in solid state, is unique for each ore and for each chemical composition of the system being assayed.

The culture and bio-oxidation of mineral compounds in the conditions described below were carried out by using the strains indicated in Table II, by way of example and not limitation. (Some of these strains were isolated from minerals from the Argentina deposits "Bajo de la Alumbrera" and "Campana Mahuida").

TABLE II

Strains Capable of Bio-oxidating Mineral Compounds

| Strains | Considered as | Origin | Already Tested or Known Substrates | Optimum Temperature Range |
|---|---|---|---|---|
| ATCC 19.859 | *Thiobacillus ferrooxidans* | *T. ferrooxidans* ATCC 19.859 | $Fe^{2+}$, $S°$, $S_2O^{2-}$, $S_4O^{2-}$ | 28–37° C. |
| $BA_1$ | *Thiobacillus ferrooxidans* like microorganism | Isolated from copper mineral from "Bajo de la Alumbrera" deposit | $Fe^{2+}$, CuS, $Cu_2S$, $FeS_2$, PbS, Zns, $Sb_2S_3$, CoS | 28–37° C. |
| $BA_2$ | Same as $BA_1$ | Isolated from copper mineral from "Bajo de la Alumbrera" | $Fe^{2+}$, mineral sulphide | 28–37° C. |
| $BA_3$ | Facultative Thermophilic bacterium similar to thiobacilli | Same as above | $Fe^{2+}$, mineral sulphide | 40–50° C. |
| SA | Facultative Thermophilic bacterium of the genus sulfobacillus | Isolated from a sample of soils rich with sulphur compounds | $S°$, $S_2O^{2-}$, CuS, ZnS | 37–60° C. |
| $CM_1$ | *Thibacillus ferroxidans* like micro-organism | Isolated from copper mineral from "Campana Mahuida" deposit | $Fe^{2+}$, CuS, $Cu_2S$, $FeS_2$, CoS, PbS, ZnS, $Sb_2S_3$ | 28–37° C. |
| $CM_2$ | Facultative Thermophilic bacterium similar to thiobacilli | Same as above | Same as above | 28–45° C. |
| CRT | Sulfolobus like microorganism | It was detected as a temperature resistant contaminant growing in sulphides sterilized with flowing steam | CuS, ZnS, PbS, $Sb_2S_3$ | 70–100° C. |

The development of studies and ideas relating to the present invention will be presented below:

Preliminary Studies of the Growth in Ferrous Agarized Medium

*T. ferrooxidans* is the bacterium most commonly used in Biometallurgy. Although microorganisms like *T. ferrooxidans* use numerous insoluble sulphur compounds, in addition to ferrous iron, the solubility of ferrous iron has encouraged its use in agarized media for laboratory cultures.

The culture of *T. ferrooxidans* in solid agarized medium has posed many problems in the past for those desiring to obtain colonies.

Several solid ferrous media have been designed so far. All these media support the growth of colonies. However, the colonies are small, slow growing (between one and six weeks) and sometimes non-repetitive results are obtained. These difficulties have been attributed to low bacterial multiplication velocity. Besides, agar or the hydrolysis products of the agarose, used as gelling agents, are thought to inhibit growth.

Observations on the obtention of colonies in agarized ferrous medium led to the establishment of bio-oxidation conditions for sulphur compounds, which are explained below:

Petri plates prepared with a conventional ferrous medium and 0.5% agarose, and inoculated with the strains ATCC 19.859, $BA_1$ and $BA_2$, were cultivated at 30° C. and observed every six to eight hours by stereomicroscopy. For a period of approximately forty days, there was no evidence of growth. On the day the colonies appeared, the beginning of growth was observable by stereomicroscopy, and after a few hours, colonies 0.5–1 mm in diameter were clear to direct observation. If a forty-day period was required to obtain colonies due to an intrinsically low bacterial multiplication velocity, it follows that growth must have been progressive.

Petri plates placed on a slightly inclined plane were prepared with a ferrous agarized medium in order to obtain a thickness gradient of the agarized culture medium. Thus, the culture medium is thickest at one edge of the plate and thinnest at the diametrically opposite edge. The plates were inoculated by touching a location on the thicker edge with a loop holding a liquid inoculum, as indicated with an arrow in FIG. 1. At the third or fourth day, colonies were formed on the thinnest edge which is diametrically opposite to the inoculation location, as shown in FIG. 1. There was no evidence of development prior to the day which colonies were formed. In the case shown in FIG. 1, some colonies were formed even on the thin film of medium deposited over the side wall. It must be taken into account that the thinner a gel is, the quicker it is dehydrated.

A great number of tests were made varying agar or agarose concentrations and analyzing the growth according the above guidelines. It was concluded that agar or agarose does not govern the adhesion of these bacteria at the inoculation place, as it generally happens with other bacteria.

The essential condition for the formation of colonies is the adhesion of the cells to the agarized medium.

The conditions that may vary spontaneously with time in a solid agarized medium containing approximately 95% of water are the loss of water by evaporation and the resulting increase of concentration of the component salts.

Tests were carried out varying the concentrations of the component salts according to wide gradients, without observing a meaningful effect on the time of apparition of the colonies, and without any effect whatsoever on the adhesion of the cells at the inoculation place. Everything indicated that adhesion of the cells to the substrate requires a very low water content.

In tests with plates carrying equal volumes of culture medium, evenly distributed all over the plate, the dehydration degree was increased by subjecting the plates to a laminar flow hood and/or by keeping the plates at 30° C. for the spontaneous loss of water prior to inoculation. A considerable decrease in the appearance time of the colonies was observed. Using techniques combining the above-mentioned strategies with the addition of chemical agents that are known to be compatible solutes in biological osmoregulatory systems, it was possible to obtain colonies in twelve to twenty-four hours. The addition of polyethyleneglycol to decrease the water activity and the addition of surfactants, also improve the growth in agarized media.

The morphology and size of the colonies as shown in FIGS. 2–6 will depend on the strain in question, the number of inoculated cells per plate, and, essentially, on the composition of the medium and the strategy used to decrease the water activity.

However, there is a common factor for all the colonies obtained: geometrical shapes that look like crystals. This aspect was analyzed by a scanning microscope and will be described below.

Figure 5:
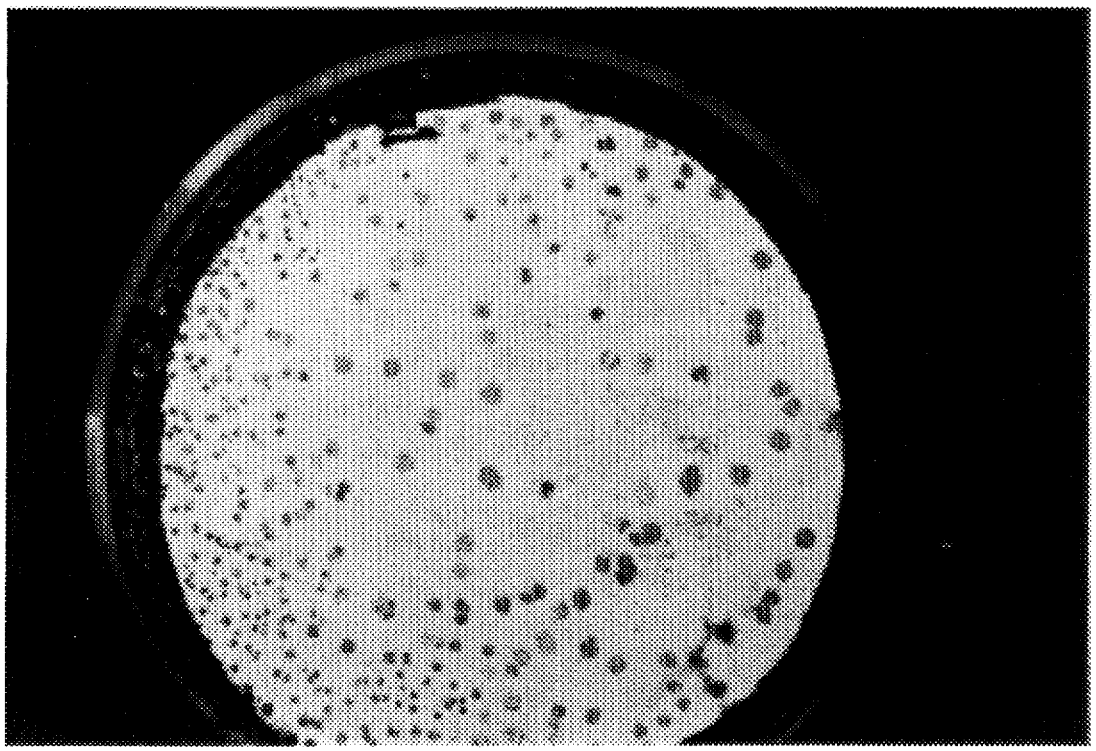
FIG. 5 shows colonies obtained in a salt deposit on the glass of a plate. The salts are the result of the dehydration of 3 cm$^3$ of a concentrated ferrous liquid medium (without gelling agent).

Considering that, in agarized media, the loss of water by evaporation is slow, an additional strategy was employed for the quick formation of colonies on a plate. 3 $cm^3$ of salt solution 10× with respect to the salt concentration of the ferrous medium used in previous tests, but without agar, were distributed per plate and then the plates were inoculated. The amount of water was less, and the evaporation velocity was higher than in the agarized media. As soon as a fine film of salts was deposited on the surface of the plate glass, and the typical brightness of excess humidity was lost, colonies developed in a few hours attached to the plate glass as illustrated in FIG. 5.

Once again, this form of culture emphasizes the capacity of adhesion and high bacterial multiplication velocity in highly dehydrated environments.

Microbian Movement Through Surfaces

The above-tests revealed that bacteria are able to move throughout the plate even on rather dry agarized media. When working with liquid inocula, it was impossible to obtain the direct attachment of the bacteria at the spot of inoculation even when the medium was highly dehydrated.

Microbial movement on humid sulphides and minerals has been also detected, as will be discussed below.

Microbial movement through an agarized surface, even when it is rather dry, and the requirement of a highly dehydrated agarized media for cell attachment and colony formation, are characteristics of the so-called gliding bacteria. They constitute a group of taxonomically heterogeneous bacteria and are believed to phytogenetically arise from different roots.

Yet, there are several characteristics that most, or all of them, have in common. More specifically, the cell wall is typically gram-negative. In many cases, a lipopolysaccharide component has been isolated and characterized. Some gliding bacteria are connected with the secretion of a mucilaginous material, causing the cells, in a liquid medium, to group or adhere to the walls of the cultivating container. These characteristics are similar to those found in bioleaching bacteria.

The environments and metabolism in which gliding bacteria have evolved favored the development of motility on surfaces. In general, they transform substrates which do not diffuse, so that the microorganisms have to roam about in order to find them. It has been demonstrated on synthetic media that gliding is essentially dependent on the humidity and concentration of nutrients.

It should be considered that microorganisms with bioleaching capacity have evolved in mineral environments where insoluble substrates are in low concentration and finely disseminated. Only the development of surface spreading mechanisms or surface translocation has allowed them to evolve.

These characteristics have an enormous potential for technological exploitation. In order to achieve high yields in the bio-oxidation of compounds that are disseminated into ores, at the moment of obtaining the required dehydration conditions to enable a stable bacterial attachment, each particle to be transformed must be in contact with at least one cell. If this is not the case, in subsequent moisturizing and dehydration stages, the cells will be allowed to move and spread to reach new particles.

Studies of Generation Times

As previously indicated, the slowness of bioleaching processes, in the conditions experimented with so far, is essentially due to the low bacterial multiplication velocity. The development of bacterial colonies in a few hours time clearly indicates that when the bacteria are attached to a solid substrate with low water activity, they multiply quickly.

The generation times of the ATCC 19.859, $BA_1$ and $BA_2$ strains were determined in order to compare them in two systems. One was a conventional ferrous liquid medium shaken at 30° C. The development was followed up by extracting daily samples, and the number of cells was determined by dilution and count in plate.

During the exponential phase corresponding to the highest multiplication velocity, the minimum generation times were determined, and they are indicated in Table III as generation times corresponding to free growth in a liquid medium.

The other system corresponds to the development of a medium of the same composition as the above, but solidified with 0.35% of agarose and highly dehydrated. The mean generation times were determined considering that each colony originates in one cell, and taking as a developing time, a period starting half an hour before the first evidence of growth was detected (by stereomicroscopy) until the moment when there were colonies clearly evident which were completely isolated with a toothpick. Each colony was suspended in a measured volume of a solution. Vortexing was carried out in order to liberate the cells. The number of cells in each colony was determined by recount in plate and considered as an average of three different colonies.

Table III indicates the mean generation times when the strains grow attached to a highly dehydrated solid medium.

TABLE III

| | Generation Times (tg) | |
|---|---|---|
| Strains | Minimum tg. Free Growth in a Liquid Medium | Mean tg. Attached Growth in a Solid Dehydrated Medium |
| ATCC 19.859 | 10 hours and 20 min. | 24 min. and 50 sec. |
| $BA_1$ | 8 hours and 27 min. | 20 min. |
| $BA_2$ | 11 hours and 32 min. | 28 min. and 15 sec. |

These results demonstrate that optimum microbial development corresponds to low water activity conditions or to a rather dry environment.

Studies of the Relationship Between Solid Product Formation and Bacteria as Evidenced by Scanning Microscopy As previously mentioned, the colonies of the tested strains have, in common, angular forms and a crystal-like appearance, although a dense bacterial population is present when they are suspended in a liquid medium and undergoing microscopic observations. As expected, the oxidized products from their metabolism, at low water activity conditions, are in solid state.

In order to examine the distribution and the bacteria-solid product relationship of such colonies, microscopic scanning was carried out.

Figure 6:
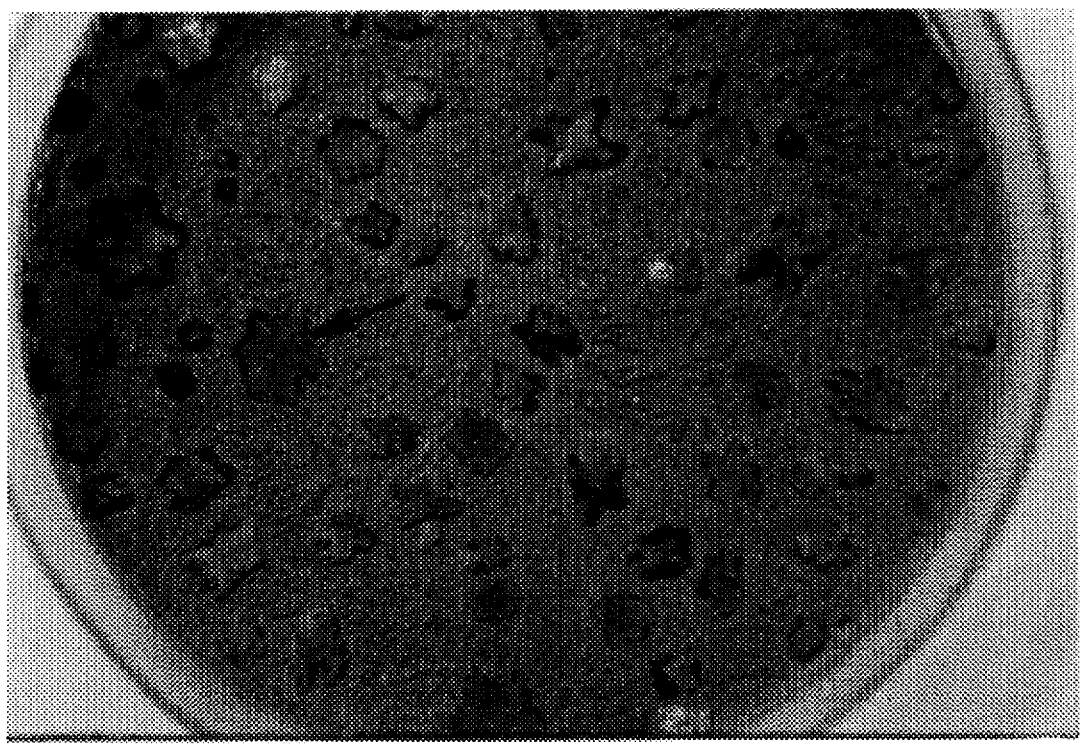

As an example, the observations made on star-shaped bacterial colonies of approximately one centimeter in diameter, such as the one indicated with an arrow in FIG. 6, will be described. These colonies were obtained from a ferrous agarized medium in which the water content was reduced according to the above described strategies.

Figure 7:
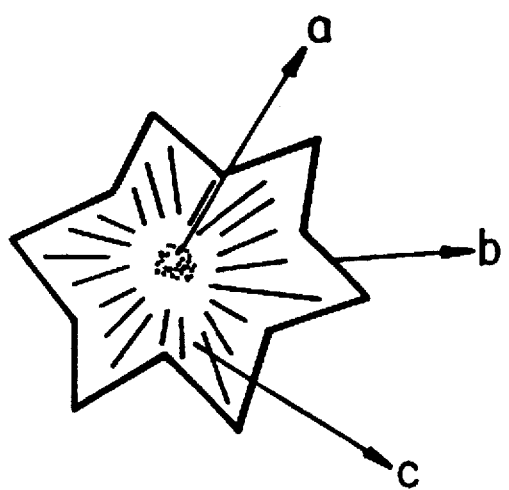
FIG. 7 shows schematically a star-shaped colony similar to that indicated with an arrow in FIG. 6, in which: (a) designates the center, (b) the border, (c) the zone between center and border.

FIG. 7 is a schematic drawing of a standard colony in which differentiable characteristic zones of the colony are indicated: a) center, b) border, and c) intermediate zone between center and border.

Figure 8:
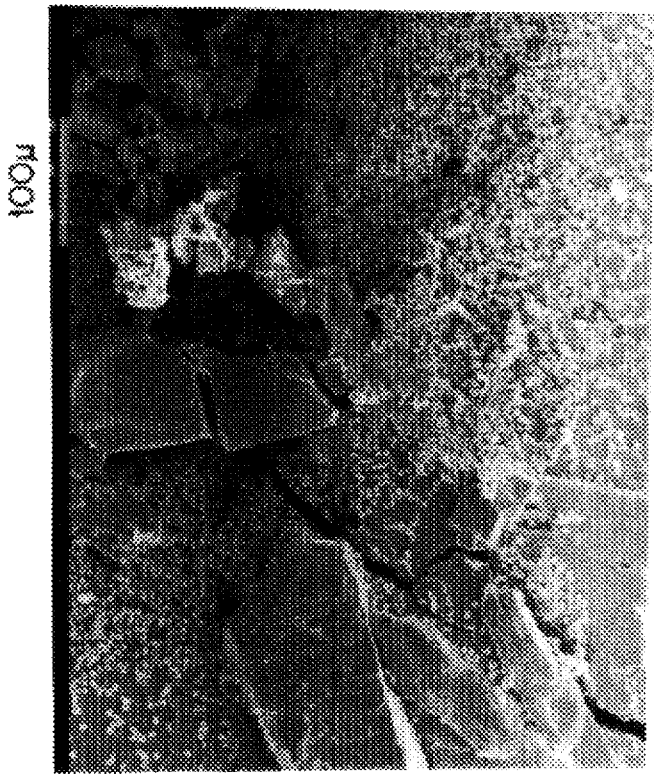
FIGS. 8, 9 and 10 are photographs obtained by scanning microscope corresponding to the center of a colony indicated with (a) in the schematic drawing of FIG. 7.
Figure 9:
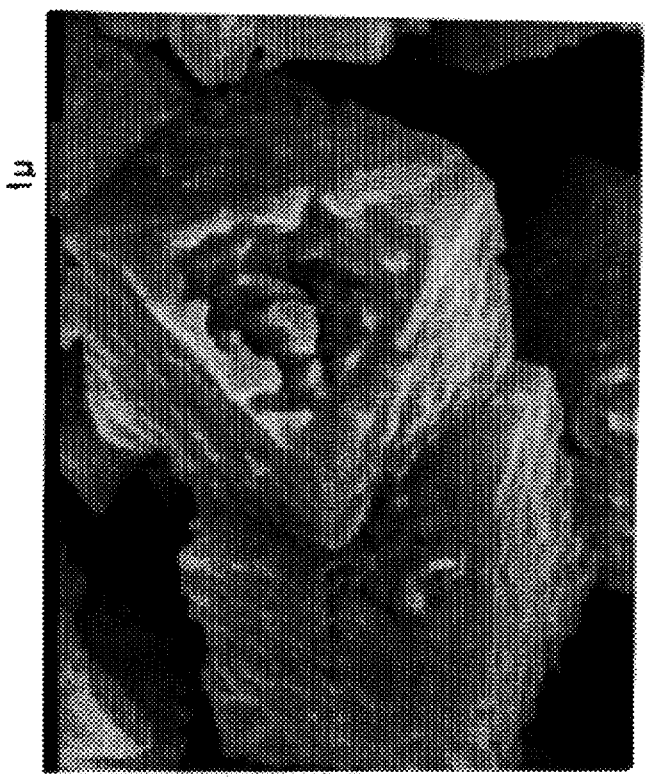
Figure 10:
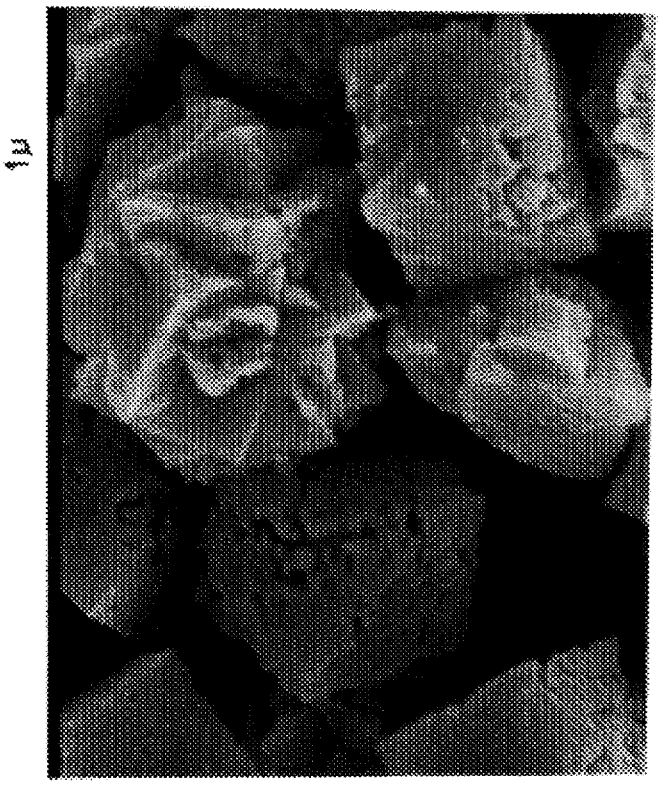

The centers of the colonies such as the one indicated with a), exhibit, under direct observation, a granular appearance or degradation. The corresponding scanning photographs show minor units of disintegrated cubic form, as shown in FIG. 8, with their walls severely perforated as shown in FIGS. 9 and 10. This suggests that the bacteria remain temporarily occluded in the solid product they form. Afterwards, they perforate the solid product and abandon it.

Figure 11:
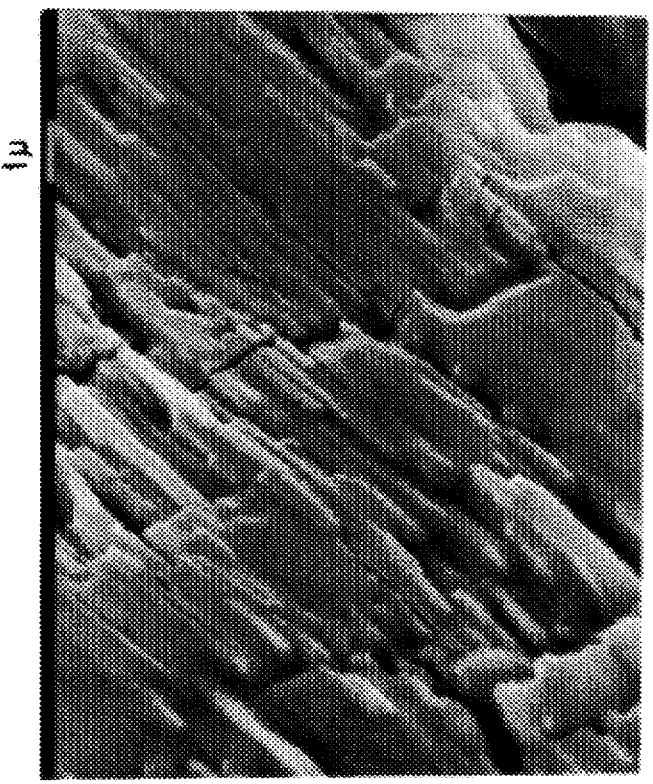
FIGS. 11, 12 and 13 are photographs obtained by scanning microscope corresponding to the zone of a colony indicated with (c) in the schematic drawing of FIG. 7.
Figure 12:
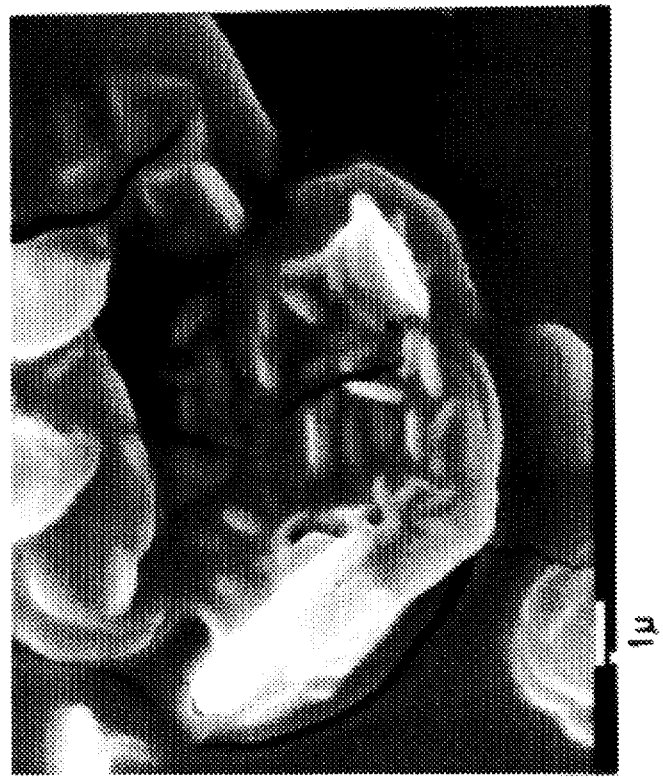
Figure 13:
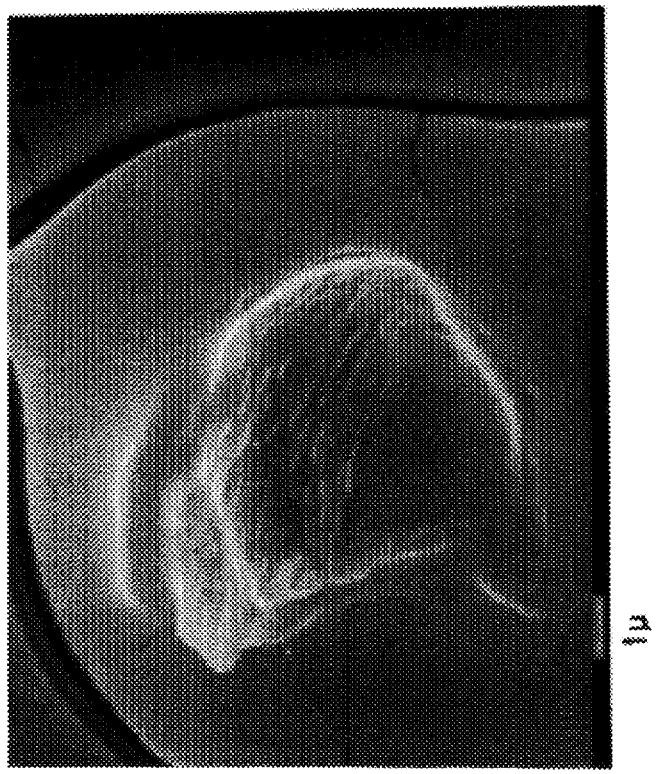

When the surface of the zone between the center and the border, as represented by c) in FIG. 7, was examined by scanning, only a solid compound appearing like crystals ordered parallel to the plane of the colony was observed, as shown in FIG. 11. However, if a colony is washed with a slightly acid 1° C. solution prior to fixing for analysis by scanning, bacteria in the inside can be observed without an organized distribution, as shown in FIG. 12. However, if the crystal-like solid from this zone is destroyed mechanically with a sterile toothpick prior to observation by scanning, the bacteria appears distributed in planes and in ordered directions, as shown in FIG. 13.

Figure 14:
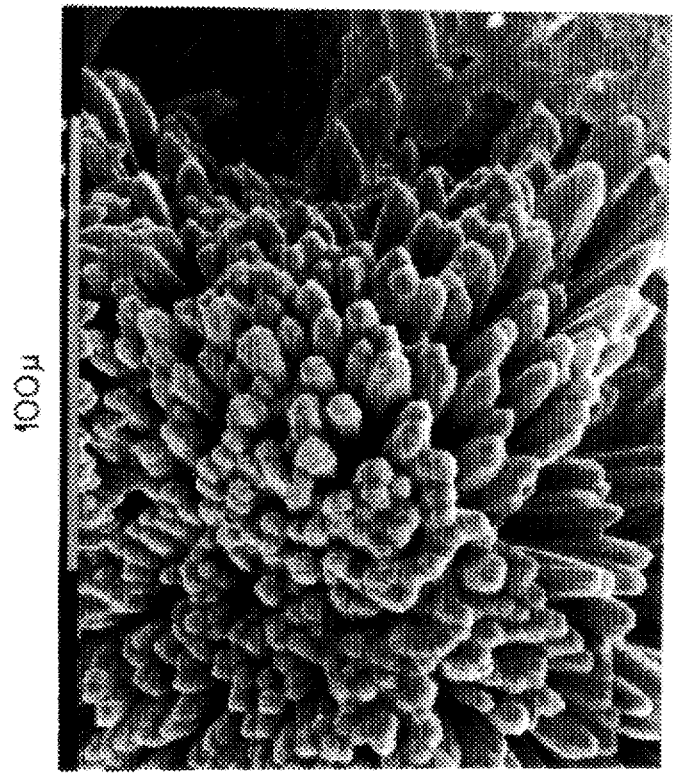
FIGS. 14, 15, 16, 17 and 18 are photographs obtained by scanning microscope corresponding to the border of a colony, indicated with (b) in the schematic drawing of FIG. 7.
Figure 15:
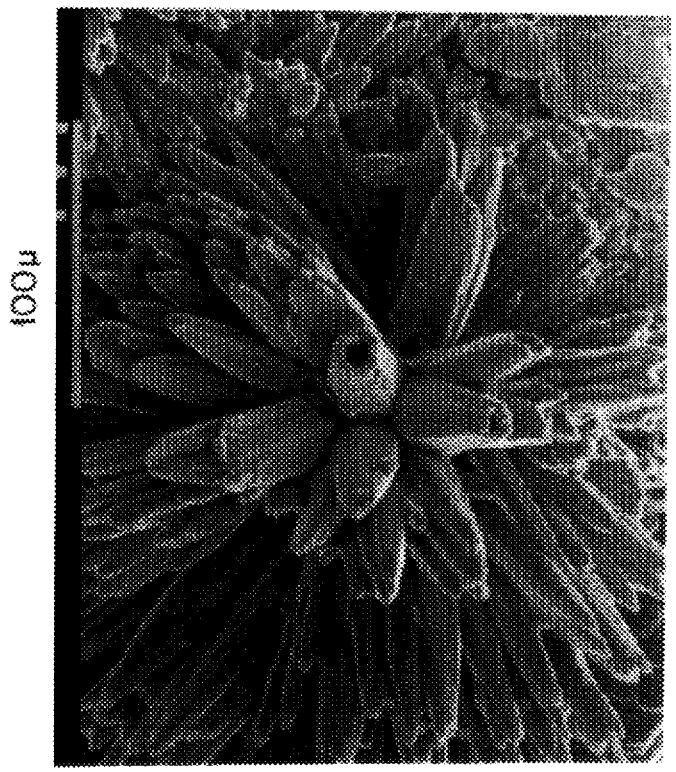
Figure 16:
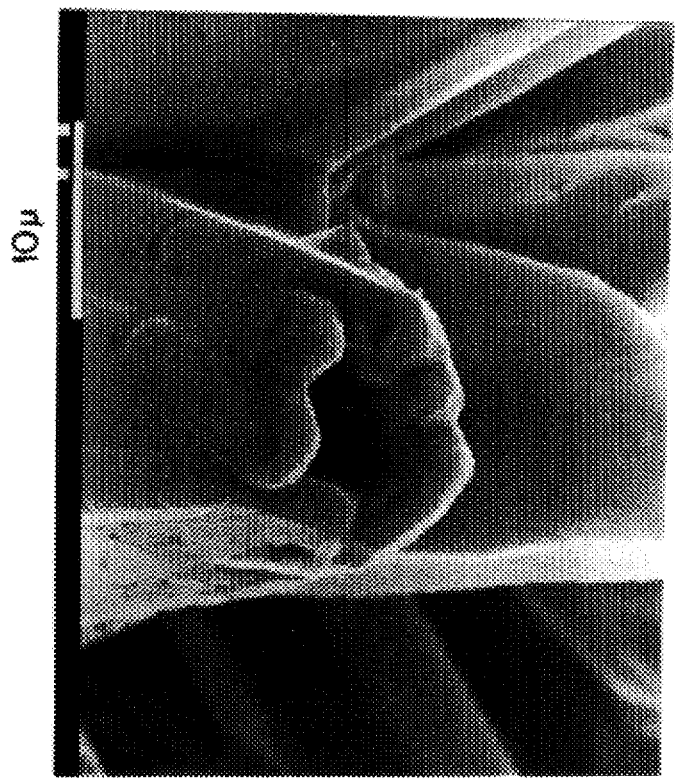
Figure 17:
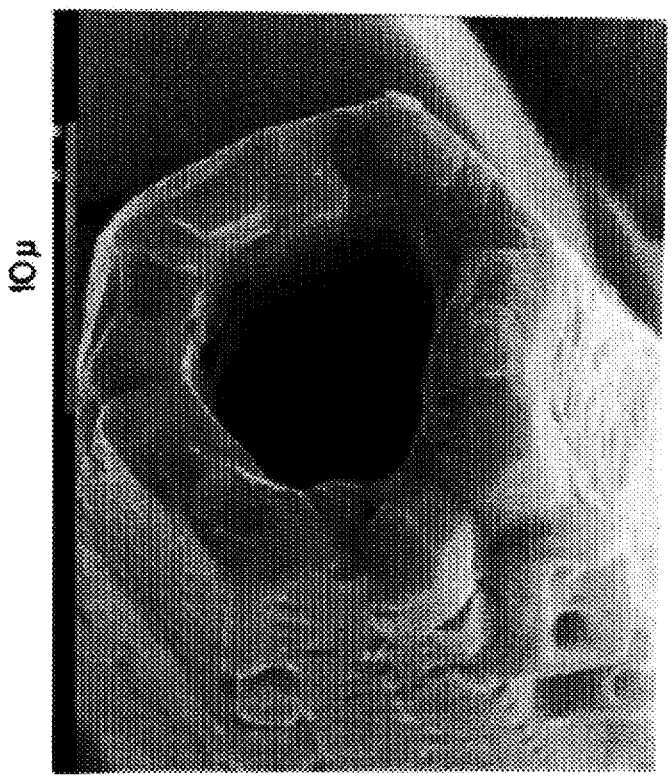
Figure 18:
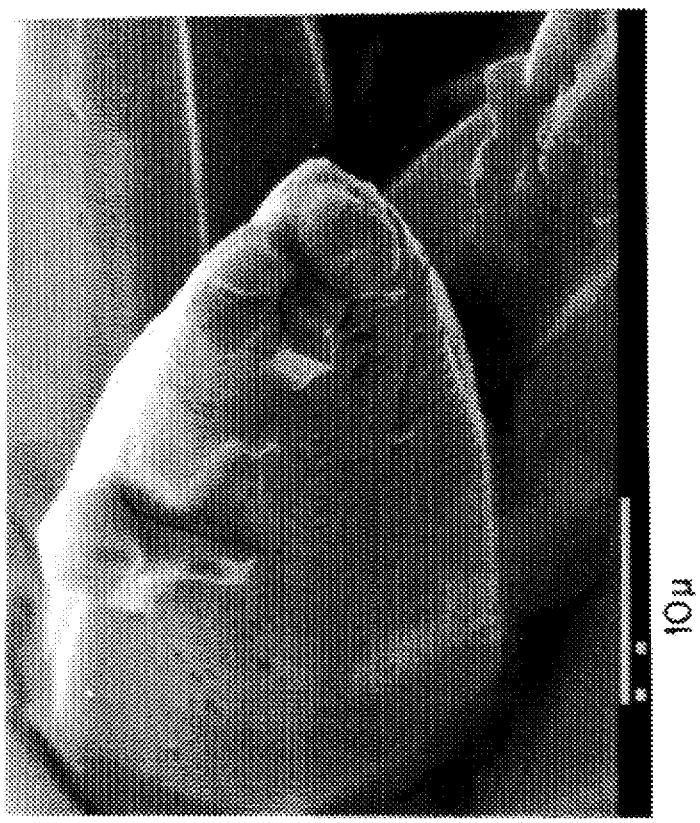

When the border of the colony indicated as b) in FIG. 7 is analyzed by scanning without introducing any previous alteration, crystal-like bodies are observed. These differ from those of zone c) because they stand up from the plane of the colony, and groups of them adopt the form of a cluster, as shown in FIGS. 14 and 15. Although all the bodies from the border have a similar form, differences among them can be seen basically at their upper extremity which is more exposed to air and remote from the base. Some of these bodies have their upper extremities closed, but others are opened, as shown in FIGS. 16 and 17. Some of the bodies show fractures on the upper extremities as shown in FIG. 18.

Observations carried out in the border of the colonies, together with the fact that 24 to 48 hours after the analyzed colonies were obtained, minor colonies began to form in the surroundings of the original ones without any evidence of communication through the substrate, permit associating the phenomenon to a kind of bacterial surface translocation known in microbiology as "darting". It is produced by the expansive forces developed in an aggregate of cells inside a common capsule and results in the ejection of cells from the aggregate.

Bacterial Development in Relation to the Nitrogen Source

Although bioleaching bacteria are extremely efficient in scavenging nitrogen in the form of ammonia, the scarcity of nitrogen in leach liquors may limit the efficiency of bacterial leaching operations. On the other hand, the addition of ammonia to leaching solutions, implies an additional cost.

The ability to fix nitrogen is important for any organism inhabiting environments deprived of nitrogen. It has been demonstrated that at least $T.\ ferrooxidans$ is capable of fixing atmospheric nitrogen in limited conditions of oxygen supply, and this microorganism has been characterized as having a nitrogenase system, and nif or nitrogen fixation genes from this system have been cloned.

However, in situ studies have not demonstrated nitrogen fixing activity in heap leaching operations. Although the physiological conditions under which nitrogen is fixed vary, the nitrogenase enzyme is conserved and is usually sensitive to oxygen. The nif proteins are oxygen-labile, and the system responsible for nitrogen fixation has been found to function only when protected from oxygen.

The physiology of an obligate aerobe microorganism which possesses a nitrogenase system has been a biological contradiction that, until now, had not been solved. Nevertheless, it was thought that if bacteria had evolved with a nitrogenase system, conditions must exist in which this system functions efficiently.

The growth of microorganisms with bio-oxidation capacity, indicated in Table II, using synthetic sulphides as substrate, and under the conditions mentioned below (which are characterized by low water activity) and which result in the corresponding oxidized solid, crystal-like products containing the bacteria, is totally independent from the addition of nitrogen.

As corroboration of the nitrogen source and the elements required for microbial growth, although present in small quantities (such as phosphorus, potassium, magnesium), the bacterial development was analyzed in relation to the medium composition using analytic grade ferrous sulfate as the energetic substrate.

In order to introduce in the analysis system the lowest possible quantity of components, and considering that gelling agents may bring impurities, the method of colony formation in the salts deposited on the plate glass, was used.

Plates, nine centimeters in diameter, were prepared. One of the following media was distributed on each plate:

a) 3 ml of an analytic grade $SO_4Fe.7H_2O$ 10% solution, adjusted to pH=1.8 b) 1.5 ml of an analytic grade $SO_4Fe.7H_2O$ 20% solution adjusted to pH=1.8, plus 1.5 ml of a solution adjusted to pH=1.8 containing: KCl, 0.1 g; $K_2HPO_4$, 0.25 g; $M_gSO_4.7H_2O$, 0.25 g; $Ca(NO_3)_2$ 0.01 g; $H_2O$, 800 ml.

Figure 19:
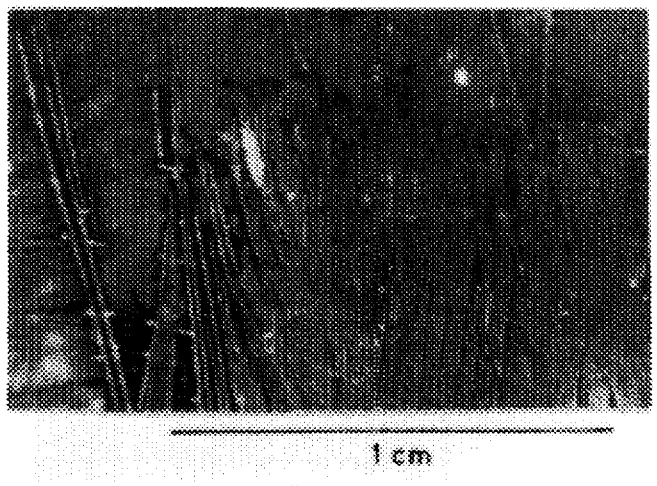
FIG. 19 shows the typical tracks of a bacterial surface translocation mechanism, by which bacteria move in groups, called "social gliding". It was produced in a film of analytic grade ferrous sulphate deposited on a plate glass.

Different strains gave equivalent results. In the plates containing only analytic grade ferrous sulfate, there was no colony formation. In some cases, the typical slime tracks of a kind of bacterial surface translocation called "social gliding" remained engraved, as shown in FIG. 19. It is known that this phenomenon is induced by nutrient deficiency.

Figure 20:
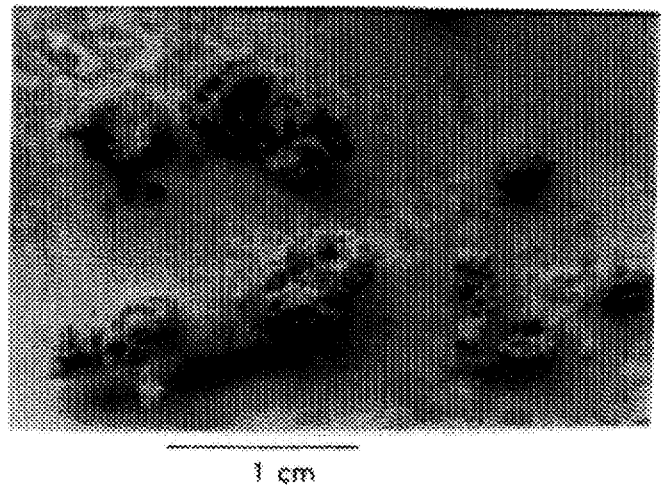
FIG. 20 shows the colonies obtained in a film of salts containing, in addition to ferrous sulphate, other salts required for bacterial development.

In the plates containing, besides ferrous sulphate, small quantities of salts which provide life-supporting elements, colonies of approximately 5 mm developed, as shown in FIG. 20. A nitrogen source was not added.

This suggests that in highly dehydrated conditions, the nitrogenase system is efficient for fixing atmospheric nitrogen. It appears that the solid product in which the bacteria remain occluded, at least temporarily, protects the nitrogenase system for oxygen.

Microbial Development and Bio-Oxidation of Sulphide Minerals

The principles described previously with respect to bioleaching bacteria in relation to water, were applied to bio-oxidation of synthetic sulphides, natural specimens, concentrates and other ores.

A weighted and sterile quantity of each substrate in question was placed on Petri plates and homogeneously distributed on all the surfaces. Afterwards, the substrate was moisturized with a sulphuric acid solution, the most convenient volume and concentration of which were determined for each particular case:

The most convenient volume per mass unit of the substrate under consideration is the minimum volume that ensures the total and homogeneous acidification of the substrate.

This volume will depend on the physical and chemical characteristics of each particular substrate and, in the case of porous minerals, acidification through the pores must be ensured. Nevertheless, the volume must be as small as possible in order to decrease the losses of time inherent to the subsequent dehydration of the substrate.

The most convenient concentration of acid is the amount of acid which, in the most convenient volume, ensures neutralization of the mineral, prevents compaction, provides the amount of acid for an efficient bacterial development, and contemplates possible losses of acid by evaporation.

Criteria established in respect to the optimum pH for microbial growth in liquid media, are not valid for the development conditions here proposed for several reasons.

The acidification volume is much smaller than the volume of acid solutions provided in liquid systems. If the acid concentrations were the same or equivalent, the availability of acid would be very low in this new system. The metabolic conditions, and probably the cellular surface composition of the bacteria in such diverse environments, are different. Also, when the system reaches the high dehydration degree required for quick bacterial development, the pH concept is not applicable.

It should be mentioned that the existing impurities in natural specimens, and even in the synthetic sulphides tested, were generally enough to provide the required small quantities of elements essential for bacterial growth (i.e., phosphorus, potassium, magnesium, etc.). Nevertheless, this must be analyzed for each substrate.

The plates were inoculated with any of the strains indicated in Table II and subsequently incubated in such a way as to facilitate a quick loss of water by evaporation. This water was introduced during the acidification. In all cases, when the substrate acquired a dry appearance, the microbial development associated with the corresponding bio-oxidated solid product was obtained in a few hours.

Figure 21:
FIG. 21 shows blue colonies of a crystalline appearance obtained in acidified synthetic CuS by inoculating the $BA_2$ strain. It was incubated at 30° C.
Figure 22:
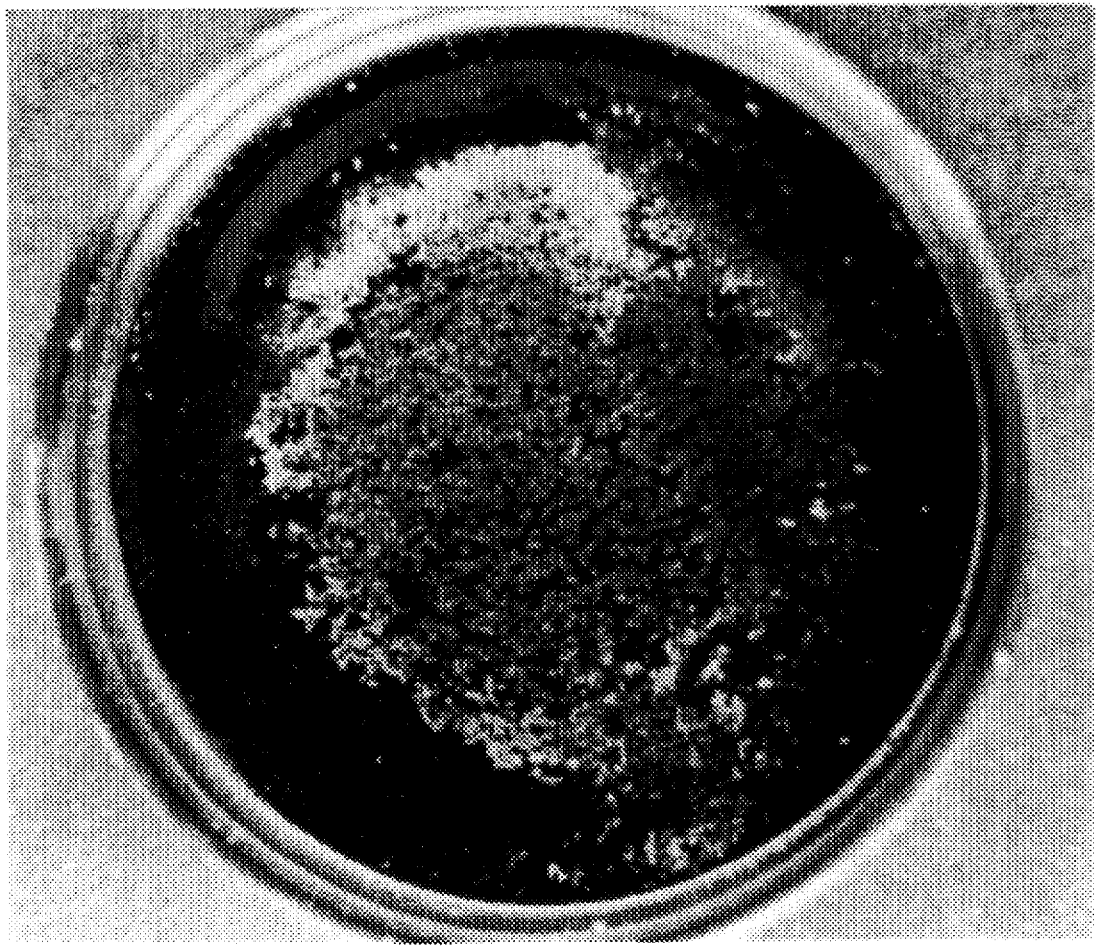
FIG. 22 shows a bacterial development associated with light blue crystals in a plate with acidified CuS. It was obtained by inoculating. The center of the plate with a concentrated suspension of the $BA_3$ strain. The plate was cultivated at 37° C. keeping the plate half open.
Figure 23:
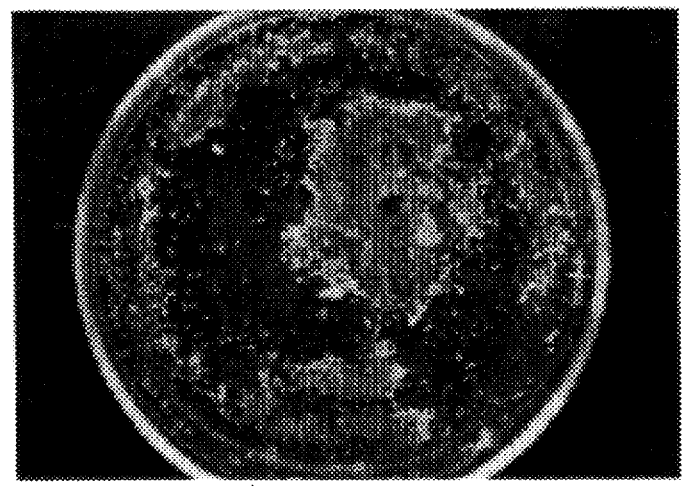
FIG. 23 shows a bacterial development associated with light blue crystals in a plate with acidified synthetic CuS that was inoculated with the CRT strain. It was incubated at 85° C.
Figure 24:
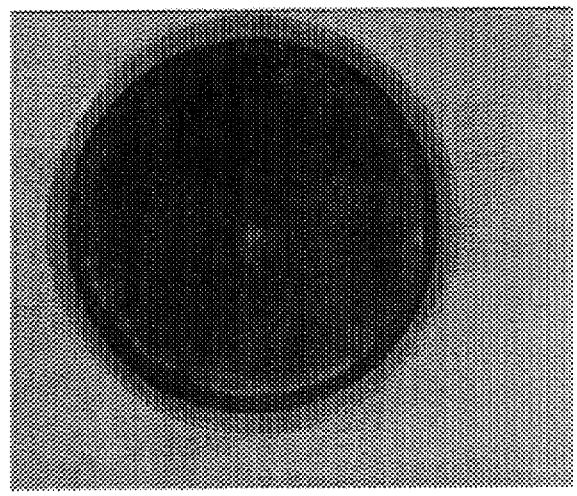
FIG. 24 shows colonies of the $CM_1$ strain associated with soluble iron compounds, obtained by using, as substrate, a natural pyrite specimen of high purity, crushed to −100 mesh. It was incubated at 300° C.
Figure 25:
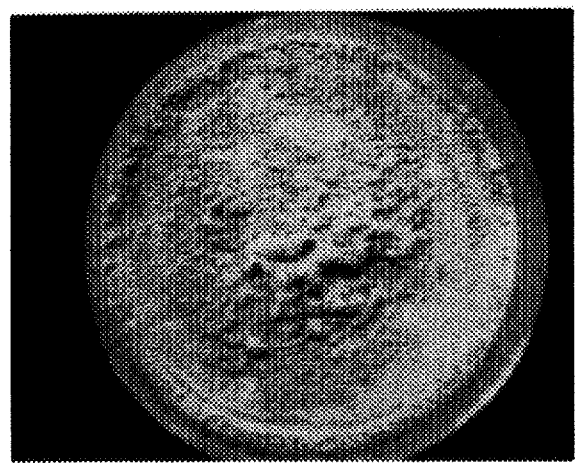
FIG. 25 shows a bacterial development associated with the white color of zinc sulphate, obtained by using an acidified sphalerite concentrate as substrate. It was inoculated with the ATCC 19.859 strain and incubated at 30° C.
Figure 26:
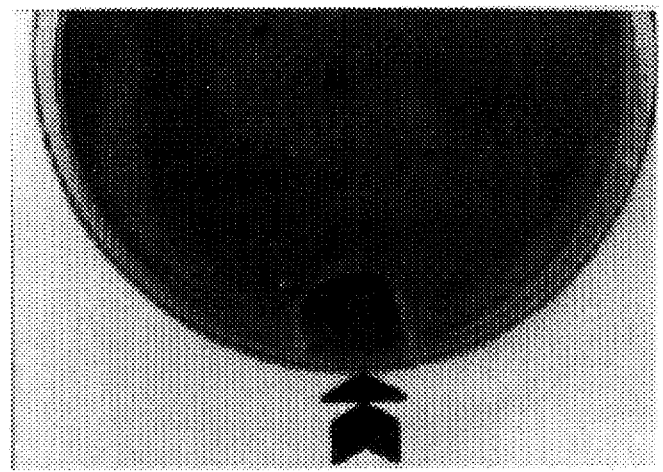
FIG. 26 illustrates a plate prepared in the same way as the one in FIG. 25. It was dehydrated until 90% of the water added during the acidification was lost. It was inoculated with a liquid inoculum in the spot indicated with the arrow.
Figure 27:
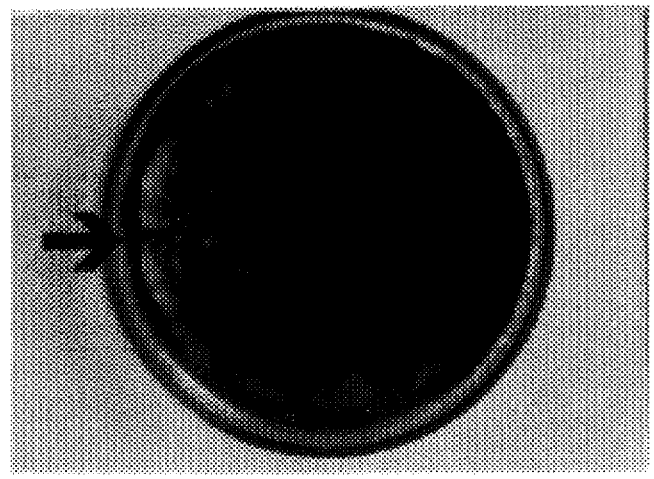
FIG. 27 shows a bacterial development associated to zinc sulphate, in the inoculation place indicated with the arrow. The plate was inoculated with the CRT strain, from a solid culture. The plate was incubated at 96° C. keeping the plate halfway open.

Tests using different substrates, which are not limitative, will now be described.

a) A thin layer of dry and sterile synthetic copper sulphide was distributed in a Petri plate, 9 cm in diameter. Next, it was acidified adding, drop by drop, 1.5 cm$^3$ of a sterile 0.1N solution of sulphuric acid. It was inoculated in the center of the plate with 10 microliters of an inoculum of the $BA_2$ strain prepared by dissolution of a copper sulphate crystal from a previous culture in a 0.06N solution of sulphuric acid. The inoculum was prepared at the time of inoculating the new plate in order to keep the bacteria in a liquid medium during the least possible time. It was incubated at 30° C. When the substrate acquired a dry appearance, the first evidences of development were observed, and a few hours later, blue crystals of copper sulphate were obtained. They were 0.5 cm wide by 1.5 to 2.5 cm long, as shown in FIG. 21. These crystals, are themselves, bacterial colonies.

b) A plate prepared as in a) was inoculated at the center with 20 microliters of a dense inoculum of the $BA_3$ strain and was cultivated at 37° C. keeping the plate halfway open in order to facilitate the loss of water by evaporation. After twelve hours, a development, as illustrated in FIG. 22, was obtained. The results manifest the bacterial movement capacity while humidity was present.

c) A plate prepared as before was acidified by adding 2 cm$^3$ of a 0.06N solution of sulphuric acid. It was inoculated with 10 microliters of an inoculum of the CRT strain prepared as previously described and incubated at 85° C. After six hours, the first evidence of development were detected. Two hours later, a development as the one shown in FIG. 23 was obtained.

d) A natural pyrite specimen ($FeS_2$) of high degree of purity, crushed to –100 mesh when dehydrated after acidification, was used as a substrate. It showed a high tendency for compaction impeding bacterial development. It was determined that by using a 1:1 ratio between the weight of pyrite and the acidification volume, the most convenient concentration of acid is 0.45N. Thus, by placing 0.5 g of sterile pyrite on a plastic plate (5.5 cm in diameter) and adding 0.5 ml of a sterile 0.45N solution of sulphuric acid, and by rotating movements, a fine homogenous layer of acidified substrate was obtained. The center of the plate was inoculated with an inoculum of the $CM_1$ strain adapted for growing in pyrite by previous cultures. Keeping the plate closed, it was incubated at 30° C. In these conditions, twenty four hours were required for the substrate to acquire a dry appearance. At this time, the first evidence of development was observed and ten hours later, a development as shown in FIG. 24 was obtained.

e) A natural galena specimen (PbS) of high degree of purity, crushed to –40 mesh, was used as substrate. 1 g of sterile galena was placed on a plastic plate of 5.5 cm in diameter. It was acidified with 1 ml of a sterile 0.24N solution of sulphuric acid, and it was inoculated with the $CM_2$ strain from a previous culture in CuS. It was incubated at 37° C. Between 18 and 22 hours later, the beginning of growth was detected. Six hours later, glassy white bodies with a crystalline appearance were obtained. The size was the same as the galena grain but contrasting with the grayish tone of the latter. It was determined, by microscopic observation, that the white bodies carried a dense bacterial population.

f) 2 g of the same substrate as in e) were placed in a glass plate. 2 ml of a 3.0N solution of sulphuric acid were added. The plate was inoculated with a CRT strain. The plate was incubated at 90° C. After six hours, the first evidences of development were observed. Four hours later, white solid bodies of similar characteristics as those described in e) were obtained.

g) A concentrate of sphalerite (ZnS) containing 56% of zinc was used as substrate. 2 g were placed on a plastic plate 9 cm in diameter. 1.5 ml of a sterile 0.24N solution of sulphuric acid was added. By rotating movements, the acidified substrate was distributed throughout the plate. The center of the plate was inoculated with the ATCC 19.859 strain previously adapted to growth in ZnS and suspended in $SO_4H_2$ 0.06N at the moment of inoculation. The plate was incubated at 30° C., and the plate was kept closed. About 48 hours later, the first evidences of development were observed, and twelve hours afterwards the development shown in FIG. 25 was obtained, associated with the typical white color of zinc sulphate.

h) A plate prepared in the same way as in g) but without inoculation was incubated at 30° C. until 90% of the water introduced during acidification was lost (as determined by loss of weight). After that, it was inoculated with a liquid inoculum, in the place indicated by the arrow in FIG. 26. Twelve hours later the typically white development was obtained in the surrounding area of the inoculation spot. No development was observed in the inoculation spot which had a higher degree of humidity due to the inoculum. This indicates that the bacterium moves from the most humid area to the less humid area where it is attached, transforming the substrate.

i) A glass plate carrying 2 g of the same concentrate of sphalerite (ZnS) as the one used in g) and h) was acidified with 2 ml of a sterile 0.18N solution of sulphuric acid. It was inoculated with the CRT strain from a previous culture in ZnS. Instead of suspending the inoculum in a solution, the inoculation was carried out by direct transfer, (with a thick needle) of solid zinc sulphate to a marked edge of the plate indicated with an arrow in FIG. 26. It was incubated at 96° C. with the plate half open to enable the quick loss of humidity. After two hours, the first signs of development were detected and two hours later, a development associated to the typical white color of zinc sulphate was obtained in the inoculation area, as shown in FIG. 27.

j) A natural antimonite $Sb_2S_3$ specimen of high purity degree, crushed to −100 mesh was used as substrate. Of the substrates tested, this one was the hardest to acidify because of its hydrophobicity. Obtaining a homogenous acidified pulp distributed on the surface of the plates required higher volumes of acid solution than in previous cases. Besides, in order to obtain a homogenous pulp, a sterile spatula should be used when mixing on the plate. This system also had a high tendency to compact which obstructs bacteria development. This explains the need to use higher concentrations of acid than in previous cases.

Figure 28:
FIG. 28 shows the development of the $BA_2$ strain, using a natural specimen of $Sb_2S_3$ as substrate. It was incubated at 30° C.

A wide variety of tests were carried out to determine the most convenient volume and acid concentration. For any of the strains indicated in Table II, the best results were obtained by homogeneously distributing 0.5 g of $Sb_2 S_3$ and 1.5 ml of an acid solution 0.6N in polystyrene plates, 5.5 cm in diameter. It was incubated at 30° C. keeping the plates open to enable the loss of water by evaporation. Between 3 and 4 days later microbial development took place associated with the deliquescent white bio-oxidation product in solid state, as shown in FIG. 28. It is possible to reduce the volume of the acidification solution by adding tensoactive agents, such as sarcosyl (1%), which furthermore enhance the microbial development. In this manner, it has been possible to obtain development in 24 to 30 hours.

k) A concentrate of molibdenite ($MoS_2$) was used as substrate. As with the prior test, this concentrate is difficult to acidify homogeneously. The obtention of an homogeneous acidified pulp, distributed on the surface of the plates, required less than 2 milliliters of sulphuric acid solution per gram of antimonite when no tensoactive agents are used. A great number of tests were carried out to determine the most convenient volume and acid concentration, and they were compared with the equivalents, but 100 microliters of a 1:50 (v:v) Nonidet $P_{40}$ solution were added which is a commercial detergent.

All the plates were inoculated with 100 microliters of a mix culture coming from the Rosario ore microflora enrichment suspended in a 0.06N sulphuric acid solution. Opened glass plates 9 cm in diameter were incubated at 30° C. In accordance with the tests without Nonidet $P_{40}$, 2 milliliters of a 2N sulphuric acid solution were required per gram of molibdenite for obtaining microbial development between 3 and 4 days later. In accordance with the tests with Nonidet $P_{40}$, 1 ml of a 0.8N sulphuric acid solution was required per gram of molibdenite for obtaining microbial development 8 hours later. In the same conditions, but without Nonidet $P_{40}$, no growth was obtained suggesting tensoactive agents act by preventing the compaction of highly hydrophobic metal sulphides which obstruct microbial development.

Figure 29:
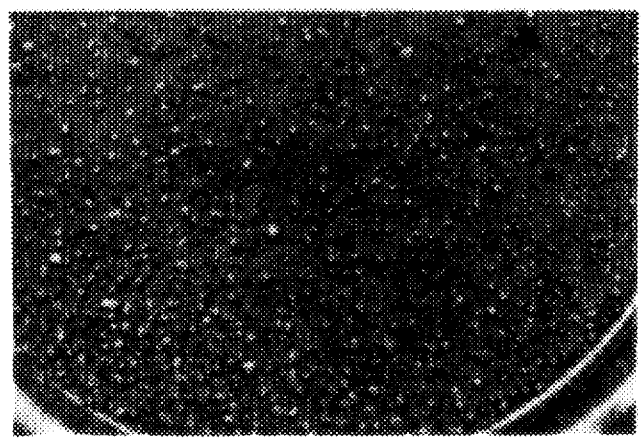
FIG. 29, 30, 31 and 32 show the red colonies obtained by inoculating acidified synthetic cobalt sulphide (CoS) with the strains ATCC 19.859, $BA_2$, $BA_1$, and $CM_1$ respectively.
Figure 30:
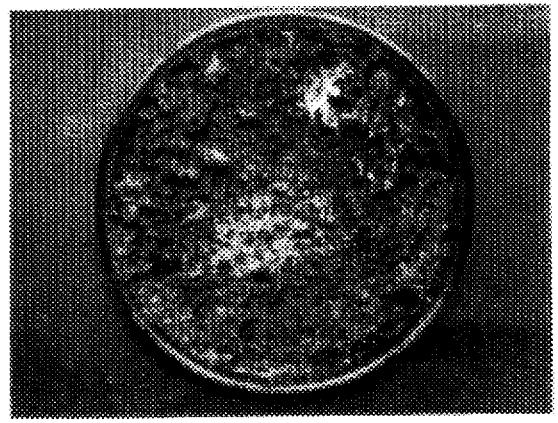
Figure 31:
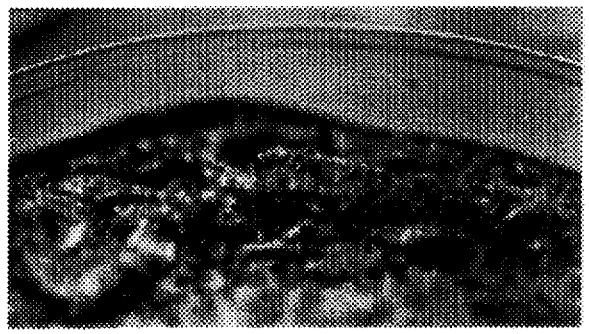
Figure 32:
Figure 33:
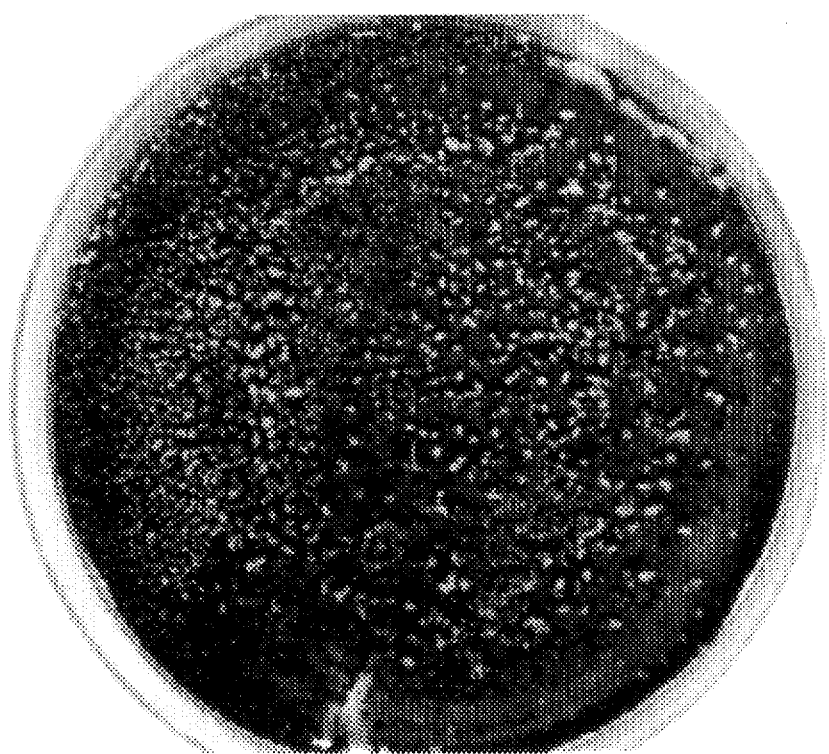
FIG. 33 and 34 show light blue colonies obtained by inoculating the $BA_1$ and $CM_1$ strains respectively, in an acidified concentrate comprising chalcocite ($Cu_2S$) and enargite ($3Cu_2S.As_2S_5$) as predominant specimens of copper. The plates were incubated at 30° C. keeping the plates open.
Figure 34:
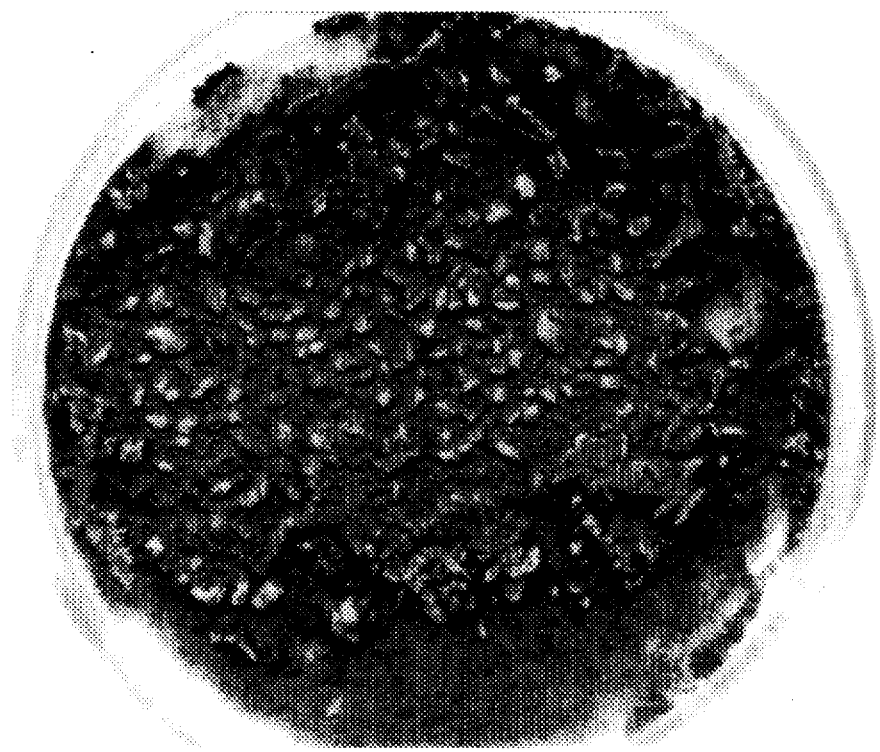
Figure 37:
FIG. 37 shows a mineral triturated to ¼ inch, comprising chalcocite ($Cu_2S$) as predominant specimen of copper, not subjected (left) and subjected (right) to bio-oxidation by the $CM_1$ strain. The plate was incubated at 37° C. for sixteen hours keeping the plate open.
Figure 38:
FIG. 38 shows the mineral subjected to bio-oxidation, according to FIG. 37.
Figure 39:
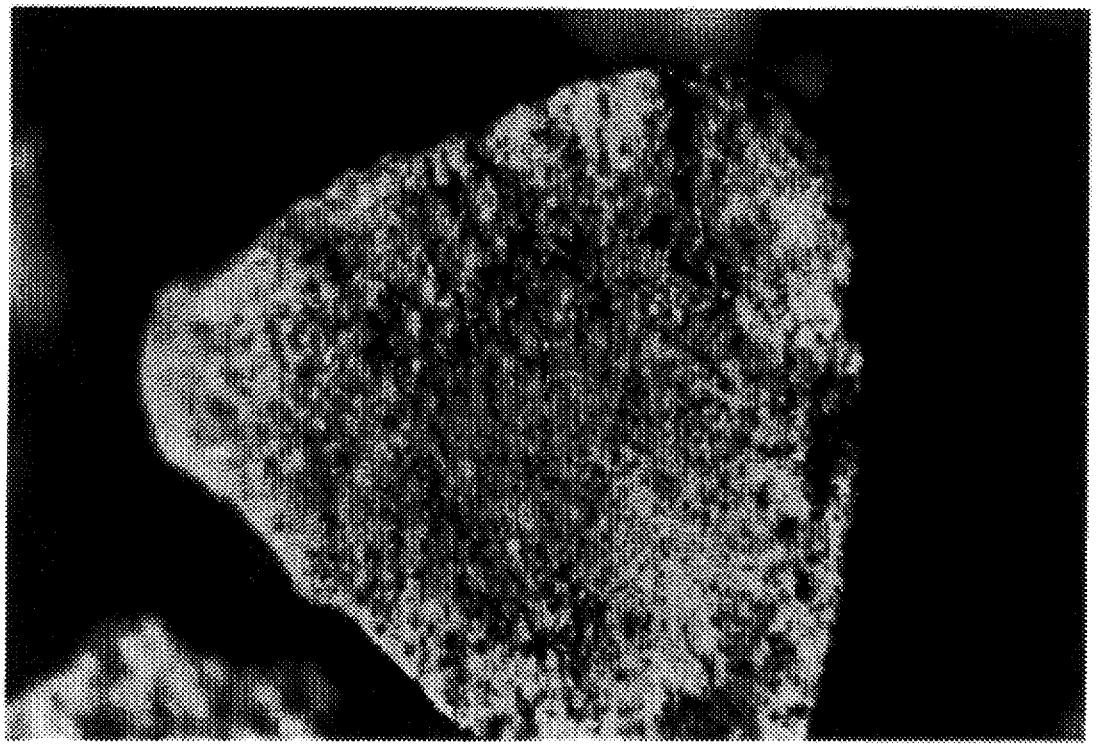
FIGS. 39 and 40 are photographs taken at a shorter distance from the bio-oxidized mineral according to FIGS. 37 and 38, in order to show the colonized mineral more clearly.
Figure 40:
Figure 41:
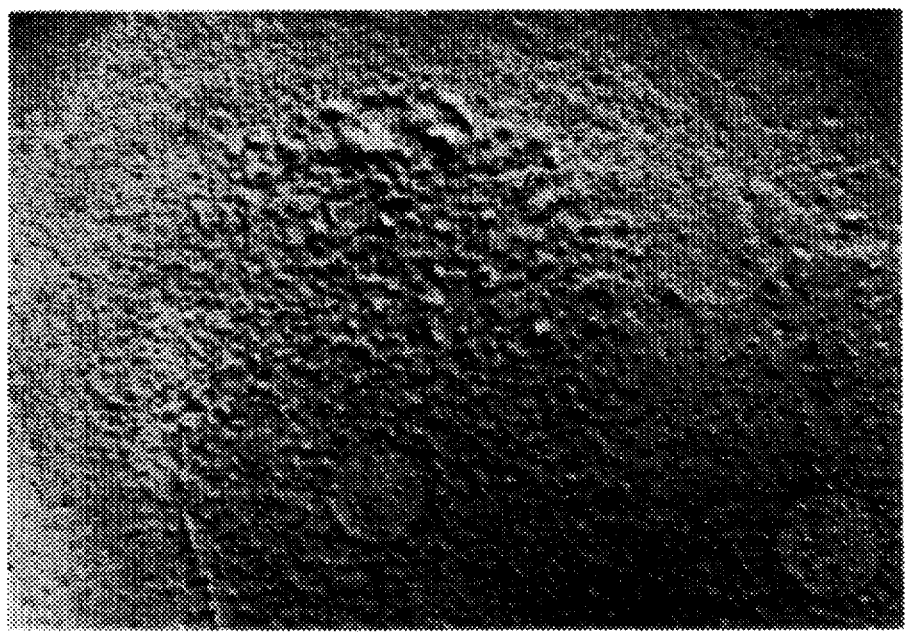
FIG. 41 shows the development of the $CM_2$ strain in a copper mineral crushed to $-100$ mesh and acidified, which contains 2.1% of chalcocite. Incubation took place at 37° C.
Figure 42:
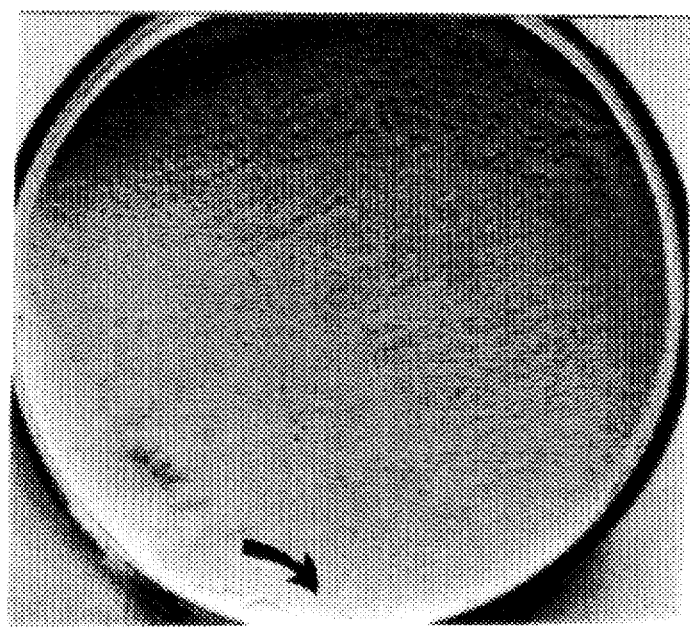
FIG. 42 shows the development of the $CM_2$ strain, in the plate area, which was first dehydrated. The arrow indicates the inoculation place. The substrate was the same as in FIG. 41.
Figure 43:
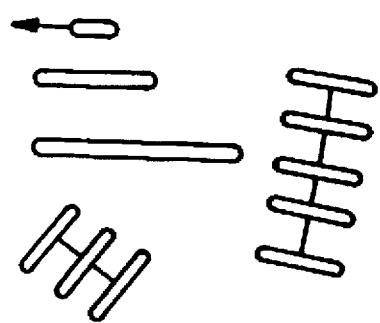
FIG. 43 is a schematic drawing of microscopic observations obtained from the suspension of a bacterial colony in a liquid medium.

Furthermore, the above-data demonstrates the possibility of using smaller liquid volume and acid concentration with the subsequent smaller required drying time when tensoactive agents are used.

l) Plates, 9 cm in diameter, were prepared with a thin layer of dry, sterile synthetic cobalt sulphide (CoS). They were acidified by adding 0.5 ml of a sterile sulphuric acid solution (0.3N) so as to acidify homogeneously all of the substrate. Plates were inoculated with different strains from previous culture in cobalt sulphide and were incubated at 30° C. Twenty four hours later, the developments shown in FIGS. 29, 30, 31 and 32 were obtained with the strains ATCC 19.859, $BA_2$, $BA_1$ and CM1, respectively. The developments presented the typical pink to red color of cobalt sulphate. The bio-oxidized product obtained in solid state may be separated by screening.

m) A copper concentrate was used as the substrate. The mineral composition, considering the base as 100% copper sulphide minerals, indicates that the predominant specimens are chalcosite (64.29%) and enargite (21.96%). 1 g was placed on each plate, 9 cm in diameter. It was acidified with 1 ml of a sulphuric acid solution 0.3N. The plates were inoculated with the $BA_1$ and $CM_1$ strains from previous cultures in the same concentrate. The plates were incubated at 30° C. and kept open. Twenty four hours later, developments as shown in FIGS. 29 were obtained. FIGS. 30 show photographs of the same developments but taken at a shorter distance.

n) A mineral from the Argentine deposit of "Campana Mahuida" comprising chalcocite ($Cu_2S$) as the predominant copper specimen, triturated to ¼ inch, was tested. 30 g of the mineral were placed in a plate, 9 cm in diameter. It was acidified by adding 20 ml of sulphuric acid solution 0.45N. It was inoculated with the $CM_1$ strain from a culture in synthetic copper sulphide. It was incubated at 37° C. keeping the plate open so as to facilitate quick dehydration. After twelve hours, when the mineral had acquired a dry appearance, the growth began. Four hours later, over the dry stones, the bacterial development associated with the oxidation of the sulphide was obtained. FIG. 37 shows the mineral non-subjected and subjected (left and right respectively) to bio-oxidation. FIG. 38 shows the bio-oxidated ore. FIGS. 39 and 40 show photographs taken at a shorter distance, of the colonized and bio-oxidated mineral.

o) A copper mineral crushed to −100 mesh comprising 2.1% of chalcocite ($Cu_2S$) was used as substrate. 5 g of sterile mineral were placed in polystyrene plates of 8.5 cm in diameter. It was acidified with 5 ml of sterile 0.4N solution of sulphuric acid and by rotating movements, the pulp was homogeneously distributed throughout the plate. 100 microliters of an inoculum of the $CM_2$ strain from a culture in CuS were distributed dropwise, and the inoculated substrate was incubated at 37° C. After 48 hours, and when the substrate had a dry appearance, the development started to appear looking like elevations in the more dehydrated edges of the plate. Twelve hours later a development, as shown in FIG. 41, was obtained. It was characterized by irregularities of the mineral layer associated with blue little crystals.

p) A plate of the same composition as the one indicated in (o) was used but it was incubated and prepared on a slightly inclined plane, so that the pulp is thinner at one edge than at the diametrically opposite edge. The pulp was inoculated at the thicker edge indicated with an arrow in FIG. 42. The plate was inoculated with 20 microliters of the same inocula mentioned in (o). It was incubated at 37° C. As expected, the thin edge was dehydrated first. After twenty six hours, the first evidence of development and microbial transformation on the thin edge was detected, and six hours later, the development shown in FIG. 42 was obtained.

Several days later, when the plate was completely dehydrated with respect to the humidity added in the acidification, there was no evidence of development in the rest of the plate. This indicates that when there is an excess of humidity, the bacteria move through the substrate, curiously in a path and associated to a negative humidity grade, producing a stable attachment on the area which is dehydrated first.

q) A low grade copper mineral sample from the "Rosario" mine, a porphyry copper deposit located in Northern Chile, was assayed. For this test, only raw mineral having a size between one and two inches was selected. The predominant copper specimen in this mineral is chalcocite, $Cu_2S$.

Figure 44:
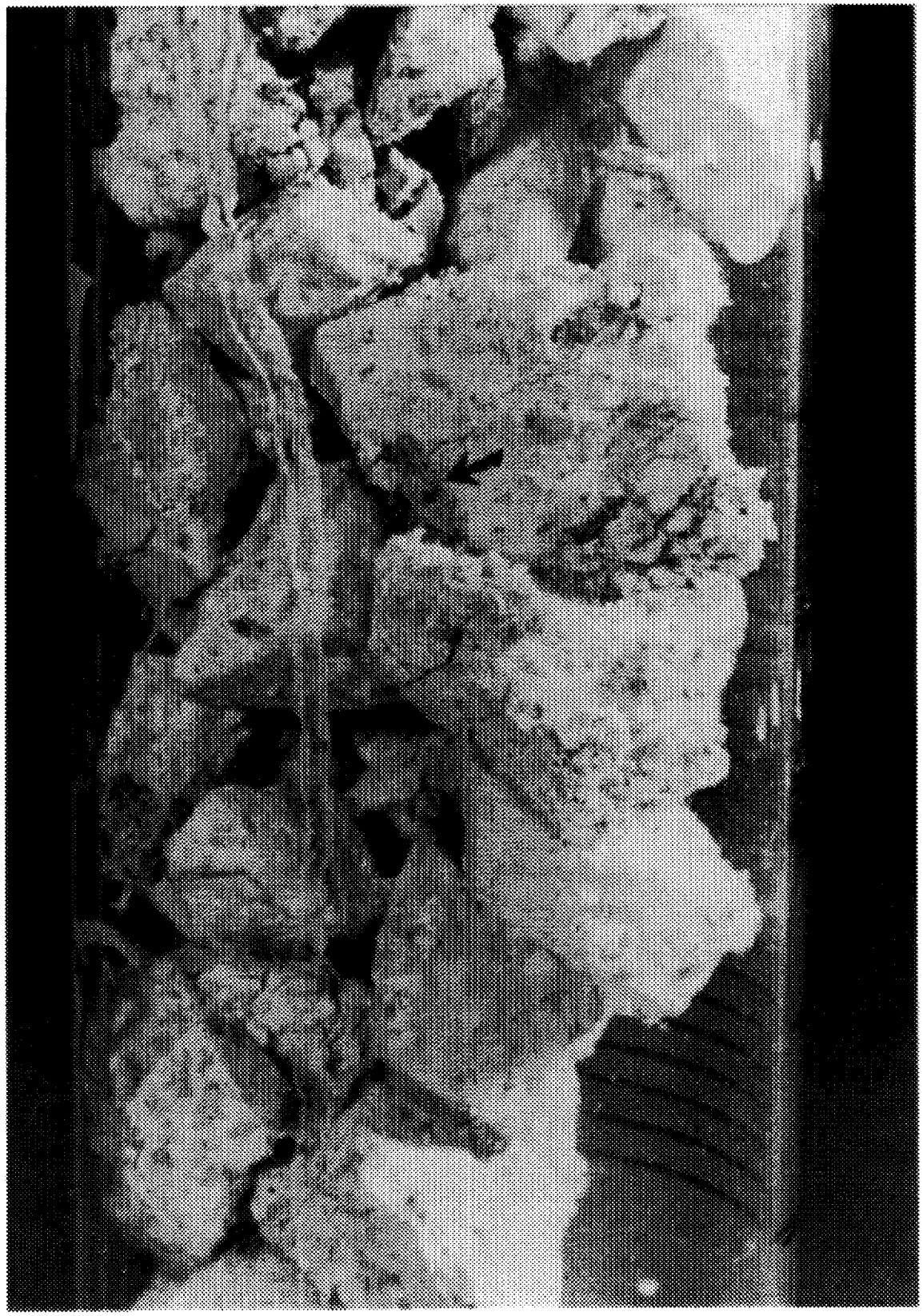
FIG. 44 is a photograph of a glass column portion, showing the bacterial growth associated with blue copper sulphate in solid state as is indicated by the arrow. The size of the mineral was between one and two inches, and after acidification and inoculation with the $CM_1$ strain, the mineral was dehydrated by exposing to the sun.

200 grams of the same mineral subjected to bio-oxidation with $CM_1$ strain, during a previous similar test, were used as the inoculum for the present test. These 200 grams were mixed and agitated with 50 milliliters of a 5N sulphuric acid solution. This mix was used for inoculation and acidification of 1,800 grams of raw ore. The initial liquid to solid ratio was 1/40. The indicated acid concentration and liquid to solid ratio have been determined as the most convenient by testing different ranges of values for both and carrying out the test in the same form as presently indicated. The mineral was placed in a glass column of 6 cm diameter and 60 cm height. The sun light lateral effect in the column was prevented by a dark plastic film wrapped around the column in such a way as to imitate what would happen if the ore should be subjected to the sun drying (being filled up with a height equivalent to the column length). When the column was subjected to the sun drying, the bacterial growth and the corresponding copper sulphate showed up as the dehydration proceeded through the column. Approximately 60 hours were necessary before the bio-oxidation reached the bottom of the column. During this drying period, the temperature varied from 19° to 35° C. FIG. 44 is a photograph of a column portion showing the bacterial colonies associated with blue copper sulphate in solid state as is indicated by the arrow.

The same photograph shows the fractures produced by the bacterial activity through the microbial growth in the internal pores of the mineral fracturing the rocks as the bio-oxidized compounds force it open. r) A mineral from the same deposit indicated in q), with chalcocite as the predominant copper specimen, was totally crushed to less than one half inch in size. 150 grams of the same ore subjected to bio-oxidation with the $BA_1$ strain, during a previous similar test, were used as the inoculum for the present test. This inoculum was mixed and agitated with 83.33 milliliters of a 5N sulphuric acid solution. This mix was used for inoculation and acidification of 1,350 grams of raw mineral by pelletization. The initial liquid to solid ratio was 1/18. The indicated acid concentration and liquid to solid ratio were determined as the most convenient by testing different values and carrying out the tests in the same form as presently indicated. The inoculated and acidified mineral was placed in a glass column 6 cm in diameter and 50 cm in height.

Figure 45:
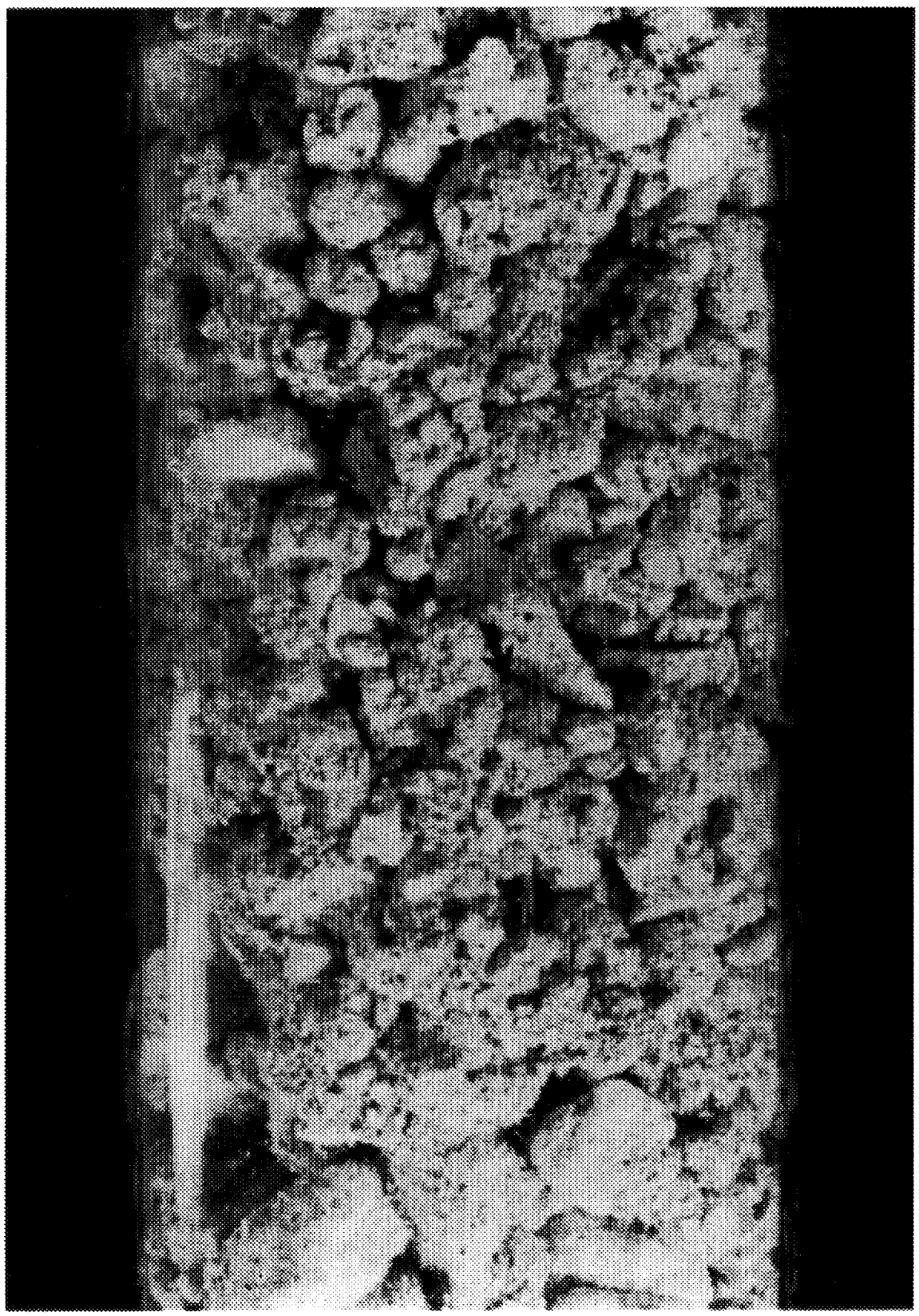
FIG. 45 is a photograph of a glass column portion showing the bacterial growth associated with blue copper sulphate in solid state, as is indicated by the arrow in a mineral crushed to less than one half inch. Pellets were obtained by agglomeration of the fines around the coarser material. After acidification and inoculation with the $BA_1$ strain, the material, placed in a glass column, was dehydrated by an air flow.

At the column base, a wire mesh was used to support the pellets. Below this mesh, a compressed air nozzle was installed in order to dose a flow of air of 10 liters per minute. The mineral temperature was around 20° C. during the test. After two hours, the first 10 cm of mineral in the lower portion of the column showed a blue microbial growth. After five hours, the microbial growth extended throughout the column. FIG. 45 is a photograph of the column with the bacterial colonies associated with blue copper sulphate in solid state, as indicated by the arrow.

s) The same mineral indicated in test r), was treated for the enrichment of its own microflora. 1,000 grams of the raw mineral was acidified by pelletizing the fine particles around the coarse ore with 66.66 milliliters of a 3N sulphuric acid solution. The liquid to solid ratio was 1/15. The prepared ore was placed in a tray of 30×30×6 centimeters and kept at ambient temperature for natural dehydration.

Between the third and the fourth day, little blue solids, looking like crystals, began to appear.

A second stage of enrichment was carried out by repeating the humectation with sulphuric acid solution and dehydration at the same conditions of the first stage. During the fourth day later, a thick blue microbial growth was obtained.

Figure 46:
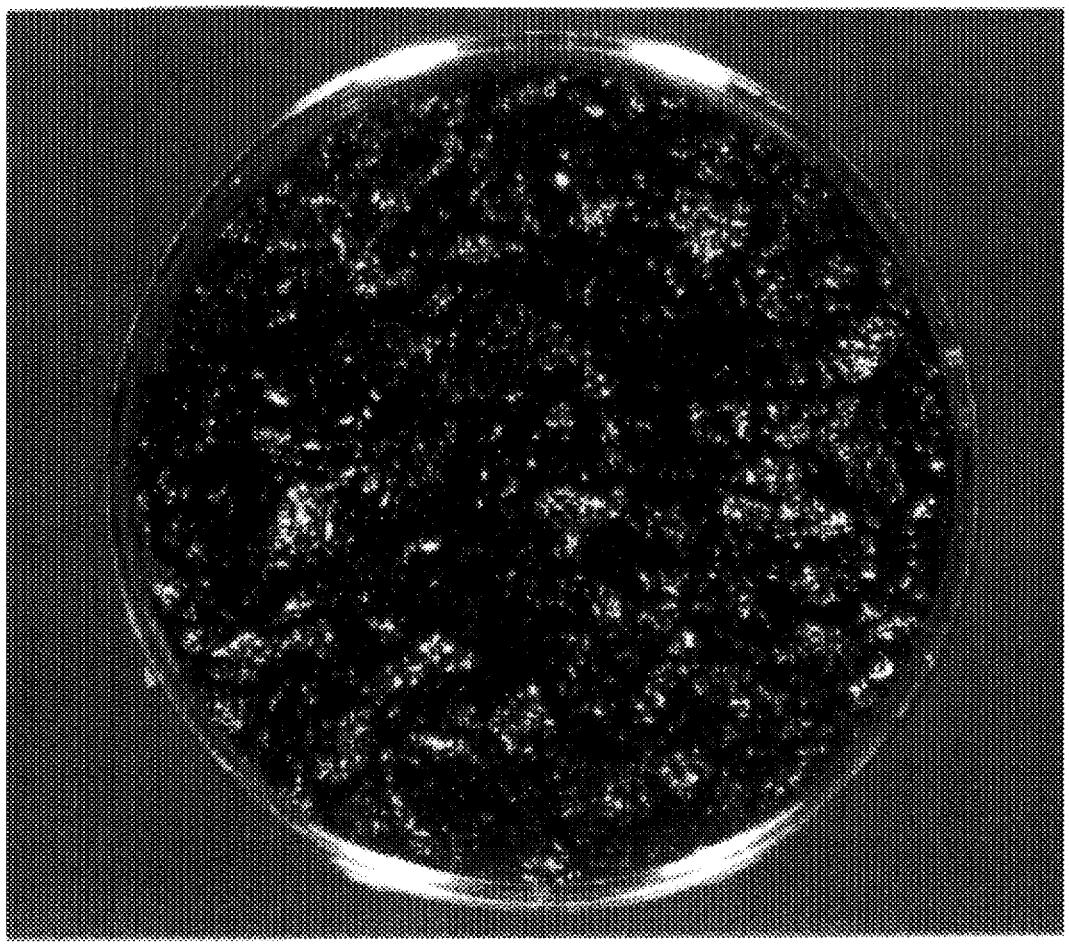
FIG. 46 is a photograph showing raw coal crushed to a size of minus half inch and FIG. 47 the same coal after a microbial treatment with the $CM_1$ strain.
Figure 47:
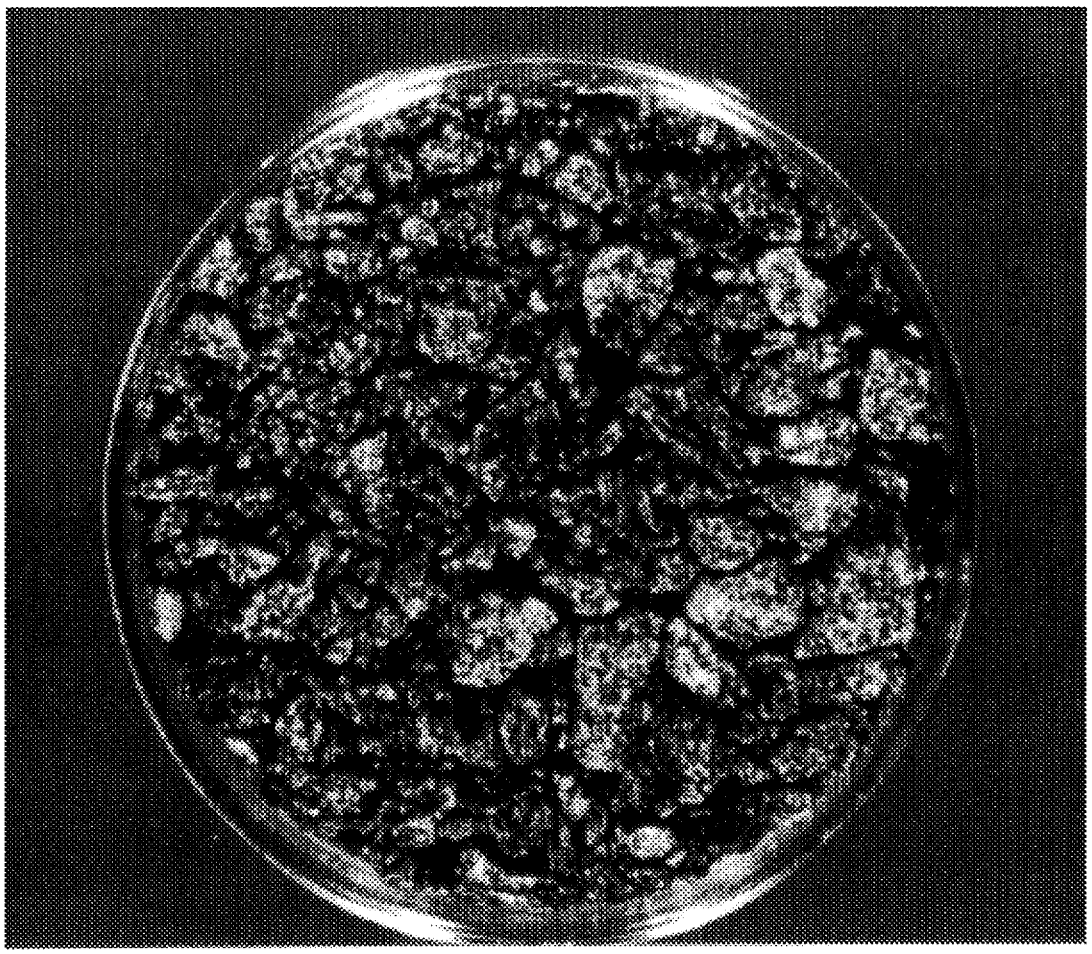

150 grams of the own microflora enriched ore, coming from the second stage of the prior enrichment, were employed as inoculum for a test carried out at in same form and under the same conditions as the test r) Equivalents features and results as the test r) were obtained.

t) A sample of coal from Cordova, Argentina, containing native sulphur and disseminated pyrite ($FeS_2$) was employed. It was crushed to minus half inch, and 200 grams were conditioned with 10 milliliters of 9K medium as a source of acid and nutrients. The initial liquid to solid ratio was 1/20. The liquid solution contained a microbial inoculum of the strain $CM_1$. The conditioned coal was placed in a vertical column of 6 cm in diameter and 15 cm in height. At the column base, a wire mesh was used for supporting the coal. The column was incubated at 30° C. The incubator had a low vertical forced air flow. As soon as the coal was being dried, starting from both sides, the bottom and the top of the column in contact with the air, the microbial growth began to develop and extended throughout the column ending in the column center. FIG. 46 shows the untreated coal. The coal taken from the column after the microbial oxidation, is shown in FIG. 47. Equivalent results are obtained with any of the strains indicated in TABLE II, by adjusting the incubator temperature inside the optimum range for each strain.

Most Relevant Conclusions Regarding the Physiology of Bioleaching Microorganisms Knowledge of the physiology of these microorganisms permits solving specific problems of optimization of the biological oxidation processes with a view to intensifying these processes.

Although substrate oxidation activity by different bacterial species, and even by different strains of the same species, is variable and determined by the prehistory of their existence, the previous requirements which must be met for the efficient biological oxidation, such as a stable substrate-cell attachment and the destruction of the sulphide mineral lattice, are governed by similar conditions.

From the previously described tests, it follows that:

1) These bacteria have evolved in mineral environments of low water content or environments that are not immersed in a liquid system. The water contained in the minerals and the humidity of the environment is enough for their development.

With regard to the suitable water content for an optimum microbial development, it must be taken into account that the microorganisms must grow and oxidize the metal sulphides. The important effect of ore particle size and the amount of moisture on the behavior pattern of solids and liquids must be considered. Clays with 20% moisture can be dry solids in aspect. Conversely, with coarser particles, moistures of 7% are wet in aspect or supersaturated in moisture. With the above observation, one can deduce that the definition of dryness is a function of the specific surface of the solid. In other words, there is a layer of solution on the solid particles' surface which produces a change when this layer becomes thin enough to allow the microorganisms to develop in a suitable environment.

The degree of moisture in mineral particles, as they occur in moist ores, concentrates, coal or other ground materials, has been defined by P. G. Kihlstedt (Consistency of Concentrates, Tenth International Mineral Processing Congress, London, 1973, paper 15). In this paper, the dry state is one in which rigid water layers may be present. The pendulary state comes into being as soon as moisture is present and is fully established at a moisture content of about 20% by volume counted on the solid matter (which for a copper concentrate is about 4% moisture when the specific gravity of the concentrate is 5 g/c.c.). All the water is bound either in rigid layers or by capillary forces. The funiculary state occurs with the addition of further water to the point where free liquid water partly fills the pores. The capillary state occurs when the pores are completely filled with water, possibly with some air bubbles entirely surrounded by water. The supersaturated state occurs when the additional water cannot find room without generating a pore pressure that once again forces the particles apart, causing them gradually to lose contact with one another.

The microbial growth with the features of the present invention generally occur below the supersaturated moisture when the water activity is not artificially reduced by the addition of chemical compounds.

2) Biological oxidation of a solid insoluble substrate implies a substrate-cell interaction through an adhesion mechanism. A stable adhesion permits the quick transformation of the substrate with a consequently high, bacterial multiplication velocity. Excess water prevents or makes such adhesion difficult.

3) If there are enzymatic systems involved on the destruction of the sulphide mineral lattice, such enzymes should not be diluted or washed out from the reacting surface.

4) In conditions of low water activity, the microbial metabolism is activated, decreasing considerably the generation times with a consequently high microbial multiplication velocity associated with a high substrate oxidation velocity.

5) Under such conditions, the microorganisms multiply, remaining occluded, at least temporarily, into the solid, crystal-like bio-oxidation product.

6) At least the tested microbial strains, when grown in a high dehydrated media, do not require the addition of a nitrogen source, suggesting an efficient fixation of atmospheric nitrogen.

7) Most of the microorganisms have mechanisms for dealing with a degree of water stress, but relatively few have evolved with physiological adaptations that enable them to grow well in low water activity ($a_w$) environments. Many terms have been used to describe these microorganisms: halophilic, osmophilic, osmotolerant, xerophytic, xerophilic, etc. Of these terms, xerophilic (from the greek= dry-loving) is perhaps the most appropriate for describing the microorganisms tested here.

The fact that these bacteria have not been analyzed in such a frame of conditions is attributed to the procedure of isolating them starting from the acid drainage of the mines. There are preconceptions that there is life only with systems having an abundance of water, without considering that these bacteria evolved transforming minerals which usually are not found in nature, suspended on a water environment and although minerals may look dry or dehydrated contain a percentage of water, at least what is at equilibrium with the humidity of the environment.

Samples of minerals that are apparently dehydrated have a rich microbial flora, especially on the surfaces exposed to the air, and they are viable cells.

Benefits Derived From the Technological Application of These Principles

The benefits of the application of the principles of the present invention will be apparent if the following is considered:

1) Under any of the systems developed heretofore in Biohydrometallurgy, for example, in tank leaching, in-situ, waste dumps and heaps, the microbial flora is compelled to develop in an aqueous environment. In such conditions, the microbial replication velocity and the substrate bio-oxidation velocity are limited. These entail long processing times, in the order of several months which create a technical and economical barrier. By application of the principles described herein, it will be possible to obtain equivalent extracting yields in terms of days. Considering that the microorganisms develop and transform their substrates in terms of hours, the total processing time is the dehydration velocity in each system and the strategy employed in the acidification as well as the proper inoculation. The least possible amount of water is incorporated into the system.

2) Considerably shorter processing times imply that for an equivalent production, much smaller processing volumes would be required with the consequent economy in capital investment.

3) The management of smaller processing volumes opens the possibility of operating precisely controlled systems.

4) Traditional systems have an important energetic cost. In tanks or reactors, pulp must be continuously shaken and aired. On other systems, the mineral is subjected to percolation of the acid leaching solutions with the attendant energy and capital costs. These costs become very important for the long processing periods required. Fast processes will imply less operational costs.

A Preferred Embodiment

In the present invention, the most convenient volume and acid concentration must be determined for each system according to the above mentioned criteria, in order to: neutralize the ore, prevent the compaction thereof, and provide the adequate environment for the microbial development.

Once the substrate is acidified and inoculated, the loss of the excess water must take place either by spontaneous evaporation, induced by a dehumidifier, or by flow of air through the ore.

The substrates to be oxidized via microbial action are found in ores and are generally disseminated in small particles. The transformation of each particle requires the attachment of at least one cell. Particles that meet the above condition at the time they reach the convenient dehydrating level will be transformed in a few hours turning into a soluble solid product which, at the same time, constitutes a microbial colony. If, at the following stage, the ore is moisturized to dissolve the already formed solid product, at least partially, the bacteria will be released and, under humid conditions, may glide or reach new particles of substrate by any other means.

The previous operations may be repeated as many times as is required in order to obtain the expected extraction yield. This will depend on the characteristics of each particular system, as well as the ore in question.

Finally, the bio-oxidated solid products must be separated by washing or by another method such us screening when a concentrate is subjected to bio-oxidation. If solubilization is used, the pH of the washing solutions will depend on the solubility of the oxidized compounds involved.

Considering that the solubilization of metal sulphides can also take place indirectly, that is, the ferric iron resulting from microbial oxidation can react chemically with sulphides oxidizing them to soluble forms, the convenience of maintaining the washing solution in contact with the mineral for a certain time, in order to permit eventual increases of the extraction yields by the indirect way, must be analyzed for each particular case.

In the case of metal bioleaching processes, the washing solutions will carry the products of interest, whereas the solids will constitute the residue. In the case of microbial purification processes, for example the desulphuration of coal or the purification of precious metals, the washing solutions will carry the residue, while the solids will constitute the product of interest.

The performance of this invention is illustrated by the following non-limiting examples:

EXAMPLES

Examples I and II illustrate the quantitative differences in biological activity of the oxidation of metallic compound in liquid media and in conditions of low water content.

Example III explains the application of the invention to a mineral.

Example IV illustrate a manner of carrying out the invention with concentrates.

Example I
Biological Oxidation Using $FeS_2$ as Substrate

A natural pyrite specimen ($FeS_2$), with a high degree of purity containing 43.5% Fe; 49.67% sulphur and 6.83% impurity, crushed to −100 mesh and sterilized in three consecutive days by flowing steam, was used as substrate.

An inoculum corresponding to the $CM_1$ strain previously adapted to growth in pyrite was used. In all cases, the corresponding sterile controls were carried out simultaneously.

The biological oxidation was tested in a conventional liquid system, with or without the addition of ammonia, and in a system of low water content in accordance with the principles of the present invention.

The biological activity was determined by measuring soluble iron by absorption spectrophotometry. The number of cells was determined by recount in plate, in agarized ferrous medium.

In the liquid medium, tests were carried out in 300 ml Erlenmeyer flasks containing 5 g of pyrite, 95 ml of sulphuric acid solution, with or without the addition of 0.3 g of ammonia sulphate, and adjusted to pH=1.7. Each flask was inoculated with 5 ml of a culture of the $CM_1$ strain containing $2 \times 10^8$ cells/ml. In sterile controls, 100 ml of solution was added instead of 95 ml. The Erlenmeyers were incubated in a shaker at 30° C.

Iron solubilization kinetics was followed by periodic determinations of soluble iron concentration in aliquots taken from the leaching solution.

The rate of iron extraction was estimated from the linear part of a plot representing the total biologically dissolved iron as a function of time and referring this value to each inoculated cell in the system.

The rate of iron solubilization was expressed as solubilized iron milligrams per hour and per inoculated cell. In the test with ammonia nitrogen, this value was $1.68 \times 10^{-9}$ mg/h cell. In the test without ammonia nitrogen, there was basically no difference with the sterile control.

For the test in dehydrated solid medium, the most convenient volume and acid concentration were previously determined. The best volume was the one corresponding to a ratio of 1:1 pyrite weight in grams to acid solution volume in milliliters. The most convenient acid concentration was 0.45N.

In order to follow up the kinetics for soluble iron, polystyrene plates (5.5 cm in diameter) were used, each containing 0.5 g of pyrite and 0.5 microliters of a sulphuric acid solution (0.45N). By rotational movements, a fine film was spread all over the surface. Each plate was inoculated with 360 cells of the $CM_1$ strain contained in 20 microliters of a sulphuric solution (0.06N). The number of cells was determined by count of colonies in plate in an agarized ferrous medium and coincided with an error of ±7% with the colonies which can be counted in pyrite plates. These plates, after reaching the highest development, were of a similar appearance to the one shown in FIG. 23. 20 microliters of a sterile sulphuric acid solution (0.06N) were added to the corresponding sterile controls. All the plates were incubated at 30° C.

Periodically, one sterile and one inoculated plate were subjected to soluble iron determination by absorption spectrophotometry. Solubilized iron by biological oxidation was plotted as a function of time.

After twenty two hours, when the plates had acquired a dry appearance, biological oxidation was initiated. Starting from twenty six hours and for a period of eight hours, the highest biological oxidation rate was obtained (i.e., $8.79 \times 10^{-4}$ mg/h) cell.

Comparing this value with the one obtained from the liquid medium with ammonia, a difference of five orders of magnitude is obtained.

Example II
Biological Oxidation Using CuS as Substrate

Synthetic CuS was used as substrate. It was inoculated with the $BA_1$ strain.

Just like in EXAMPLE I, the biological oxidation in conventional liquid medium was carried out with and without ammonia addition, and in a dehydrated solid medium according to the criteria already described. In all cases, corresponding sterile controls were conducted simultaneously. Soluble copper was determined by absorption spectrophotometry. The biological oxidation was determined in each case as the difference of solubilized copper between the inoculated system and the corresponding sterile control.

The liquid medium leaching was carried out in Erlenmeyer flasks containing 5 g of CuS and 95 ml of sulphuric acid solution, with and without the addition of 0.3 g of ammonium sulphate. The pH of the solution was adjusted to 2, and it was inoculated with 5 ml of an active culture of the $BA_1$ strain, containing $2 \times 10^8$ cel/ml. In sterile controls, 100 ml of acid solution were added instead of 95. The flasks were incubated in a shaker at 30° C.

The copper solubilization kinetics was followed up by periodical determinations of soluble copper in aliquots taken from the leaching solution. The rate of copper biological solubilization, corresponding to the linear part of a plot representing the biologically solubilized copper, as a function of time, was determined. It was expressed in milligrams of solubilized copper per hour and per inoculated cell. In the test with ammonia nitrogen this value was $5.1 \times 10^{-9}$ mg/hr cell. In the test without ammonia nitrogen, there was basically no difference with the sterile control.

For the test in dehydrated solid medium, plates, 9 cm in diameter, were prepared by adding to each one, 2 g of CuS and 2 ml of $H_2O$. A pulp was formed, and by rotational movements, it was homogeneously distributed all over the surface of the plate. The plates were dried in a laminar flux hood until attaining constant weight. 0.5 ml of a sterile 0.3N solution of sulphuric acid was added, distributing it drop by drop so as to acidify each plate homogeneously. Each plate was inoculated with approximately 40 cells of the $BA_1$ strain, contained in 20 microliters of a 0.06N solution of sulphuric acid. The number of cells contained in the inoculum (2.000 cel/ml) was by count of colonies in ferrous agarized medium, and it coincided, with an error ±8% with the number of colonies that were obtained in the plates with CuS at the end of development.

Twenty microliters of a sterile acid 0.06N solution were added to the sterile controls. All the plates were incubated at 30° C.

Soluble copper was analyzed periodically from a sterile plate and from an inoculated plate. After 18 hours, when the plates had a dry appearance, the biological oxidation was initiated and continued with an almost constant velocity during eight hours. At the end of this stage, the maximum development in terms of the size of the colonies constituted by solid crystal-like copper sulphate, was achieved.

The biological oxidation rate during this period expressed as solubilized copper per hour and per inoculated cell was 0.319 mg/hr cell. This value should be compared with the corresponding one obtained from a liquid medium.

Figure 35:
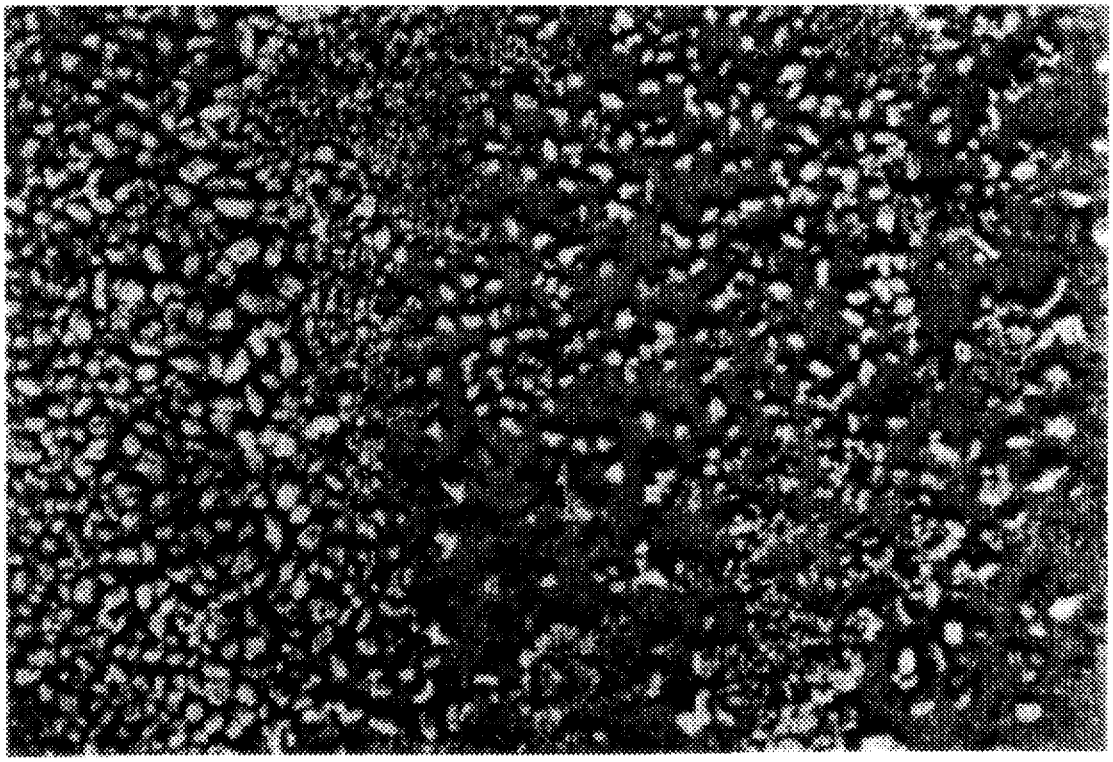
FIGS. 35 and 36 are photographs from the same plates shown in FIG. 33 and 34 respectively, which were taken at a shorter distance.
Figure 36:
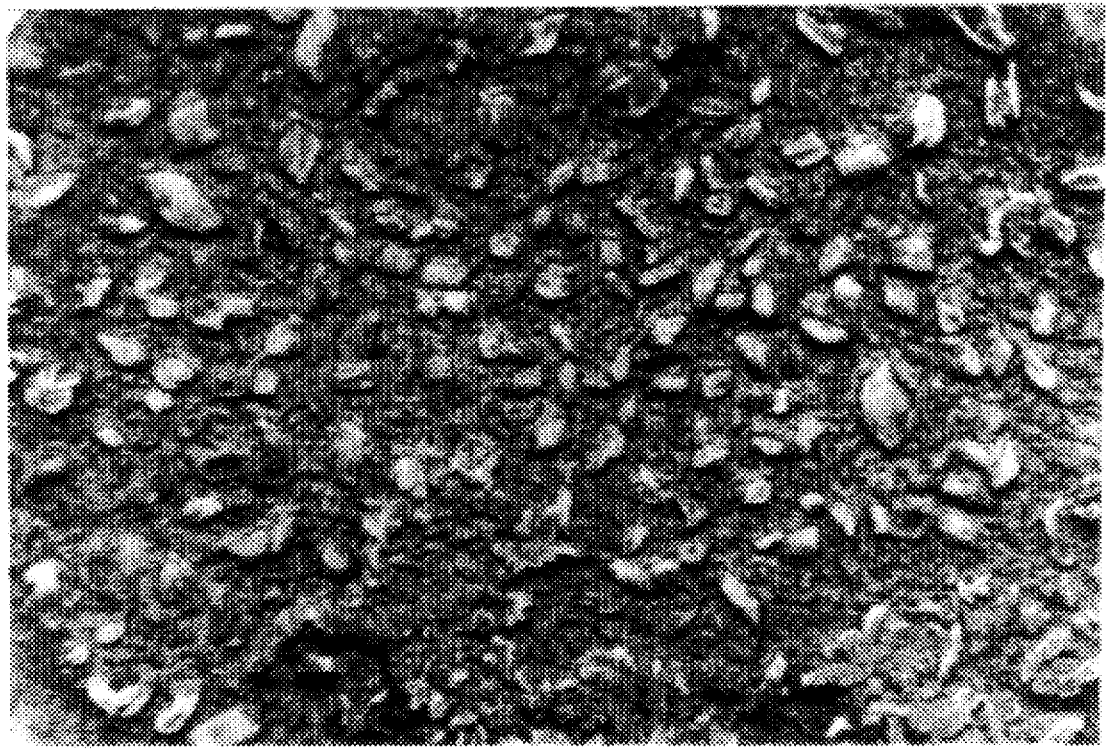

It should be noted that when a bacterial colony constituted by a solid crystal-like product is suspended in a solution, even when subjected to vortexing and is then examined with a microscope, it is possible to observe forms like the ones shown in the schematic drawing of FIG. 35: Small mobile cells, intermediate and very long non-mobile cells, and groups of cells that appear linked to each other by a very thin filament. As a consequence, at the time of determining the number of cells present in an inoculum by count of colonies in plate, it is uncertain whether each colony originates from a cell or from a group of cells. Nevertheless, considering that the applied inoculum in the corresponding liquid and solid medium have the same origin and have been treated in the same way, the biological activity values referred to inoculated cells are valid for comparison purposes, although they should not be considered as absolute values.

Example III
Bio-oxidation of a Copper Mineral Ore

The bio-oxidation of a copper mineral ore was tested, in order to determine the copper extraction yield and the necessary time to achieve it by application of the principles of the invention.

Characterization of the Mineral Ore
a. Chemical Characterization

| | |
|---|---|
| Total Copper | 1.25% |
| Soluble Copper | 0.15% |
| Total Iron | 2.66% |
| Total Sulphur | 1.78% |
| Insoluble Material | 78.50% | b. Mineralogic Characterization

The main species resulting from mineralogic analysis are listed below. The percentage of each one is expressed with reference to 100% mineral ore.

| Specie | Weights | Cu | Fe | |
|---|---|---|---|---|
| Chalcocite | 1.26 | 0.25 | 1.01 | — |
| Chalcopyrite | 0.13 | 0.05 | 0.04 | 0.04 |
| Covellite | 0.06 | 0.02 | 0.04 | — |
| Bornite | 0.01 | <<0.01 | <0.01 | <<0.01 |
| Pyrite | 2.71 | 1.45 | — | 1.26 |

It will be seen that the predominant copper specimen is chalcocite; chalcopyrite, covellite and bornite follow in order of importance.

c. Granulometric Analysis

Triturated mineral to ¼ inch was subjected to granulometric analysis using the #4, #8, #16, #40, #65, #100 screens of the Tyler series. The granulometric distribution is indicated below:

| Granulometric Distribution Tyler Series | | | Weight Retention in the Fraction | Accumulated Weight |
|---|---|---|---|---|
| | +4# | | 2.6 | 2.6 |
| −4# | +8# | | 36.7 | 39.3 |
| −8# | +16# | | 34.4 | 73.7 |
| −16# | | +40# | 9.1 | 82.2 |
| −48# | | +65# | 5.3 | 88.1 |
| −65# | | +100# | 2.2 | 90.3 |
| −100# | | | 9.7 | 100.0 | d. Natural Humidity Determination

Natural humidity was determined by loss of weight of the mineral at 100° C. until constant weight was achieved. (Corresponds to 1.5%.)

e. Acid Consumption Test

By a standard test, the sulphuric acid consumption of the mineral ore was determined. Such value corresponds to 9.9 g of acid by kilogram of mineral.

Test: Bio-oxidation on Tray

Two parallel tests were carried out on 35×45 cm stainless steel trays. Each tray was loaded with 1 kg of mineral and was treated as indicated below.

The tests took place in a closed room with a sealed door containing a dehumidifier. Water condensed by the dehumidifier was drained outside with a hose. Thus, the mineral dehydration was facilitated.

The room temperature was maintained between 28° and 32° C. during the test.

The mineral, homogeneously distributed on each tray, was acidified with 800 ml of solution containing the amount of acid determined by the consumption acid test, that is, 9.9 g of sulphuric acid.

Each tray was inoculated with 10 ml of an inoculum of the $CM_2$ strain. The inoculum was prepared by suspension in a 0.06N solution of sulphuric acid of the white zinc sulphate, development corresponding to the culture of this strain in zinc sulphide. The inoculum was prepared at the moment of inoculation and was distributed homogeneously by drops all over the tray. The trays were incubated in the above described conditions.

After twenty six hours, the mineral presented a dry aspect and a strong bacterial development associated with little light blue crystals. Basically the development was observed on the surfaces and on the sections of the mineral more exposed to air. As shown previously, the microorganisms move towards the areas which are more quickly dehydrated.

At the end of this stage, and at the end of each of the following ones, samples of 30 g of mineral were taken from each tray in order to analyze soluble copper by absorption spectrophotometry. The samples were taken with a spoon, trying to comprise all the strata established through the thickness of the ore, in order to get a representative sample.

Subsequently, three stages of humidification and dehydration were carried out. The added acid solution in each stage was homogeneously distributed with a sprinkler.

Finally, the mineral was washed keeping it in contact with the solution during six hours to enable eventual indirect increases of copper recovery. Soluble copper was determined in the filtered supernatant and the final extraction was calculated.

TABLE IV indicates relevant information concerning the operative conditions and required times in each stage and also the resultant copper extraction from each stage for the two trays.

TABLE IV also indicates the volume of the acid solution and the quantity of acid added in each stage per kilogram of mineral. In practice, a proportional volume of acid was added corresponding to the real quantity of remnant mineral, taking into account mineral samples previously removed.

It could be seen that operating under the conditions indicated in TABLE IV, it is possible to achieve a copper extraction between 66 and 68% in about three days. It is known that with conventional systems operating at similar scales, the necessary time to reach equivalent extraction yields ranges from seventy to ninety days.

TABLE V

Concentrate Chemical Composition

| Species | % weight | % copper | % iron | % sulphur |
|---|---|---|---|---|
| Chalcopyrite | 14.92 | 5.16 | 4.54 | 5.22 |
| Chalcocite | 35.62 | 28.47 | — | 7.16 |
| Covellite | 1.59 | 1.06 | — | 0.53 |
| Enargite | 0.25 | 0.12 | — | 0.08 |
| Pyrite | 33.95 | — | 15.82 | 18.13 |
| Molybdenite | 0.14 | — | — | 0.08 |
| Ganga | 13.52 | — | — | — |
| Total | 100.0 | 34.80 | 20.36 | 31.12 |

For inoculation, 110 grams of pelletized and bioxidized material with the $BA_2$ strain, during a previous similar test, were used for the present test in such a way as to inoculate the system by recycling a portion of the bioxidized product.

The material for inoculation was suspended in the acidification solution adding 40 milliliter of a 4.5N sulphuric acid solution. After this, 15 grams of calcium cloride ($CaCl_2$) were added which is employed in this case as the dehydrating agent. Then, 90 grams of concentrate were added, and when the mix was homogeneous, it was pelletized with 900 grams of quartz triturated at −4.5 +9 mesh, in such a way as to recover the quartz with a thin lamina of the prior mix.

The pelletized concentrate was placed for observation in a glass column of 6 centimeters in diameter and 30 centimeters in length. The column was kept at ambient temperature, approximately 24° C. After a few minutes, the beginning of bio-oxidation was observed as a opaque lamina covering the surface around the pellets lengthwise in the column.

Figure 48:
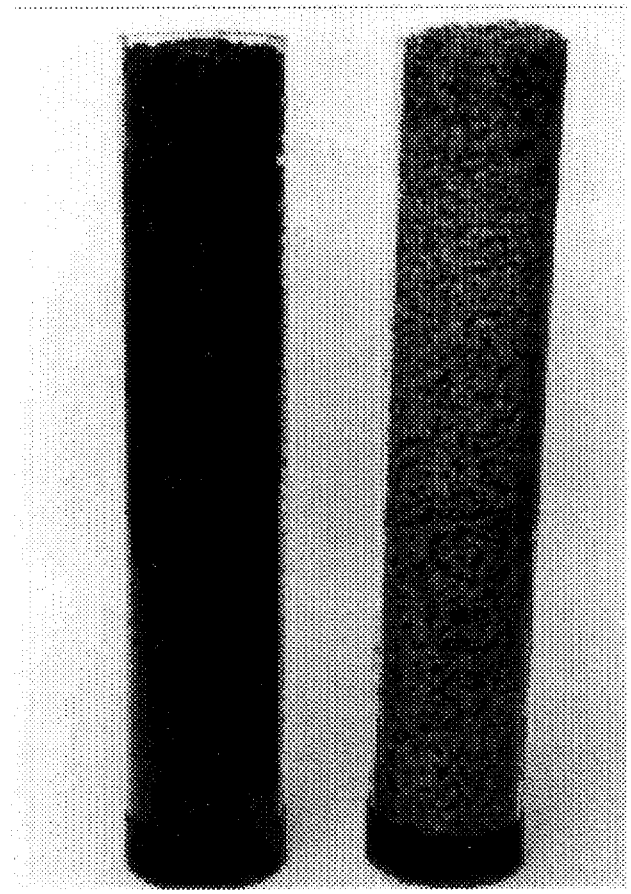
FIG. 48 is a photograph of glass columns containing a copper concentrate pelletized with quartz, using a dehydrating agent ($CaCl_2$), and inoculated with the $BA_2$ strain. On the left it is an assay at the beginning and on the right an assay 10 hours later.

The FIG. 48 shows on the left a column at the beginning of the assay and on the right a column 10 hours after the beginning.

TABLE IV

Operations Conditions and Results of Example III

| Stage | Volume of Acid Sol. (ml) | $H_2SO_4$ Partial (g) | $H_2SO_4$ Accum (g) | Time Partial (h) | Time Accum (h) | Copper % Tray A | Extrac Tray B |
|---|---|---|---|---|---|---|---|
| 1. Conditioning and dehydrat. | 800 | 9.90 | 9.90 | 26 | 26 | 26.97 | 26.10 |
| 2. Humidification and dehydrat. | 400 | 1.50 | 11.40 | 13 | 39 | 36.10 | 35.23 |
| 3. Humidification and dehydrat. | 400 | 1.25 | 12.65 | 13 | 52 | 53.90 | 52.70 |
| 4. Humidification and dehydrat. | 400 | 1.00 | 13.65 | 13 | 65 | | |
| 5. Washing | 1,000 | 1.80 | 15.45 | 6 | 71 | 63.10 | 66.35 |

Example IV
Bio-oxidation of a Copper Concentrate

This example illustrates a method of the present invention involving concentrates. Taking into account the importance of contact with air for the bio-oxidation process, the concentrate is pelletized with a course inert material in such a way as to get a high specific surface of concentrate in contact with air.

Dehydrating agents are used for decreasing the water activity in order to get a quick bio-oxidation velocity. By this manner, the requirements of drying may be reduced or eliminated according to the type and quantity of the employed dehydrating agents.

In the present example, a copper concentrate was used. The chemical composition is indicated in TABLE V.

Samples of the so bio-oxidized material were washed. Soluble copper was determined in the supernatant by atomic absorption spectrophotometry, separating the tails for the corresponding copper determination. The copper extraction was 76% in ten hours. Equivalent results had been obtained with ATCC 19.859, $BA_1$, $BA_2$, $CM_1$ and $CM_2$ strains.

It must be taken in account that the inert element for pelletization may be recycled after washing for new pelletization.

Different inert elements for pelletization have been assayed with good results, such as: triturated rocks, gravel, glass balls, plastic balls, rubber balls, etc.

Figure 49:
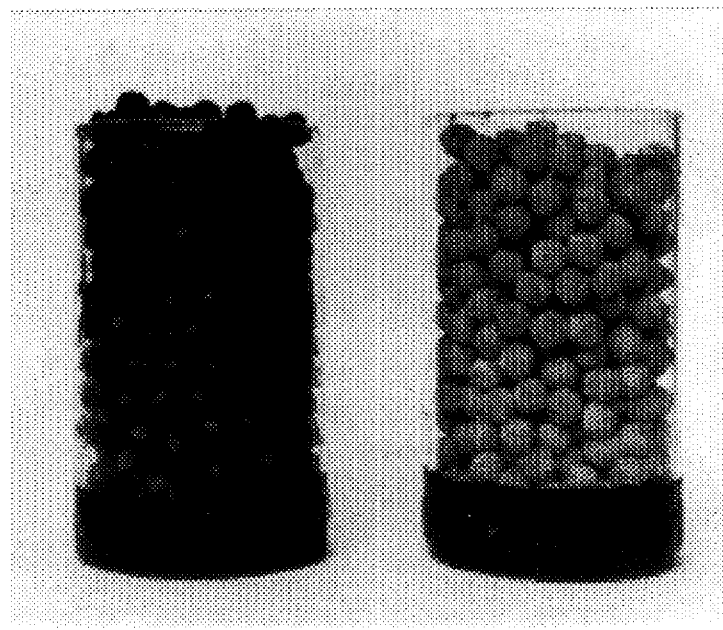
FIG. 49 is the same as FIG. 48 but the concentrate was pelletized around plastic balls and inoculated with a mix microbial culture coming from the enrichment of the Rosario mine ore microflora.

FIG. 49 shows a test with the concentrate pelletized around plastic balls. On the left, it is at the beginning and on the right, 10 hours after the beginning. Before pelletization, the concentrate was inoculated with a mixed microbial culture coming from the enrichment of the Rosario mine ore microflora, obtained as was explained in test s).

As dehydrating agents, different chemical compounds which decrease water activity have been assayed with positive results such as polyols, glycols, esters of glycols, polyglycols, polyglycol esters, polyglycol ethers, heavy metal sulphates, calcium salts, magnesium salts, silicid acid, sodium silicate, sulphuric anhydride or a mixture thereof.

The quick bio-oxidation by adding dehydrating agents to decreasing the water activity, may be too applied for ores, thereby decreasing or eliminating the drying requirements.

Nevertheless, in each case, the economy of the process must be evaluated as a function of the cost and quantity of the employed dehydrating agent as well as the economic value of the ore in question.

What is claimed is:

1. A bio-metallurgical process for bio-oxidizing in ore metal sulfides to sulphates, sulphur to sulphate, uranous oxide to uranic oxide or ferrous iron to ferric iron comprising the steps of:
   a) treating an ore with an acidic solution in an amount sufficient to prevent compaction of said ore and to provide an acidity suitable for the growth of microorganisms obtained from ore or derived from microorganisms obtained from ore, and adding an inorganic chemical compound to said acidic solution for promoting microorganism growth, which microorganisms are capable of bio-oxidizing metal sulfides, sulphur, uranous oxide and/or ferrous iron;
   b) adding to said ore a microbial inoculum containing said microorganisms;
   c) effecting removal of water from said treated and inoculated ore until a moisture content below a supersaturated moisture is obtained and until soluble bio-oxidized products in solid state and containing colonies of said microorganisms are obtained;
   d) maintaining said ore at a temperature within the growth range temperature of said microorganisms until said bio-oxidation is completed; and
   e) separating out said soluble bio-oxidized products.

2. A bio-metallurgical process for bio-oxidizing in ore metal sulfides to sulphates, sulphur to sulphate, uranous oxide to uranic oxide or ferrous iron to ferric iron comprising the steps of:
   a) treating an ore with an acidic solution in an amount sufficient to prevent compaction of said ore and to provide an acidity suitable for the growth of microorganisms present in said ore, and adding an inorganic chemical compound to said acidic solution for promoting microorganism growth, which microorganisms are capable of bio-oxidizing metal sulfides, sulphur, uranous oxide and/or ferrous iron;
   b) effecting removal of water from said treated ore until a moisture content below a supersaturated moisture is obtained and until soluble bio-oxidized products in solid state and containing colonies of said microorganisms are obtained;
   c) maintaining said ore at a temperature within the growth range temperature of said microorganisms until said bio-oxidation is completed;
   d) repeating steps a), b) and c) in a cyclical manner until a desired yield of soluble bio-oxidation product in solid state is obtained; and
   e) separating out said soluble bio-oxidized products.

3. A bio-metallurgical process for bio-oxidizing in ore metal sulfides to sulphates, sulphur to sulphate, uranous oxide to uranic oxide or ferrous iron to ferric iron comprising the steps of:
   a) treating an ore with an acidic solution in an amount sufficient to prevent compaction of said ore and to provide an acidity suitable for the growth of microorganisms obtained from ore or derived from microorganisms obtained from ore, and adding an inorganic chemical compound to said acidic solution for promoting microorganism growth, which microorganisms are capable of bio-oxidizing metal sulfides, sulphur, uranous oxide and/or ferrous iron;
   b) adding to said ore a microbial inoculum containing said microorganisms;
   c) adding to said treated and inoculated ore a dehydrating agent to effect removal of water, until a moisture content below a supersaturated moisture is obtained and until soluble bio-oxidized products in solid state and containing colonies of said microorganisms are obtained;
   d) maintaining said ore at a temperature within the growth range temperature of said microorganisms until said bio-oxidation is completed; and
   e) separating out said soluble bio-oxidized products.

4. The process of claims 1, 2 or 3, wherein said inorganic chemical compound is present in the form of a salt or an aqueous solution and said salt or aqueous solution comprises at least one element selected from the group consisting of potassium, phosphorous, magnesium, calcium and nitrogen.

5. A bio-metallurgical process for bio-oxidizing in ore metal sulfides to sulphates, sulphur to sulphate, uranous oxide to uranic oxide or ferrous iron to ferric iron comprising the steps of:
   a) treating an ore with an acidic solution in an amount sufficient to prevent compaction of said ore and to provide an acidity suitable for the growth of microorganisms obtained from ore or derived from microorganisms obtained from ore, and reducing the volume of said acidic solution by adding an agent selected from the group consisting of wetting agents, tensoactive agents, detergents and surfactants, which microorganisms are capable of bio-oxidizing metal sulfides, sulphur, uranous oxide and/or ferrous iron;
   b) adding to said ore a microbial inoculum containing said microorganisms;
   c) effecting removal of water from said treated and inoculated ore until a moisture content below a supersaturated moisture is obtained and until soluble bio-oxidized products in solid state and containing colonies of said microorganisms are obtained;
   d) maintaining said ore at a temperature within the growth range temperature of said microorganisms until said bio-oxidation is completed; and
   e) separating out said soluble bio-oxidized products.

6. A bio-metallurgical process for bio-oxidizing in ore metal sulfides to sulphates, sulphur to sulphate, uranous oxide to uranic oxide or ferrous iron to ferric iron comprising the steps of:
   a) treating an ore with an acidic solution in an amount sufficient to prevent compaction of said ore and to provide an acidity suitable for the growth of microorganisms present in said ore, and reducing the volume of said acidic solution by adding an agent selected from the group consisting of wetting agents, tensoactive agents, detergents and surfactants, which microorganisms are capable of bio-oxidizing metal sulfides, sulphur, uranous oxide and/or ferrous iron;

b) effecting removal of water from said treated ore until a moisture content below a supersaturated moisture is obtained and until soluble bio-oxidized products in solid state and containing colonies of said microorganisms are obtained;

c) maintaining said ore at a temperature within the growth range temperature of said microorganisms until said bio-oxidation is completed;

d) repeating steps a), b) and c) in a cyclical manner until a desired yield of soluble bio-oxidation product in solid state is obtained; and e) separating out said soluble bio-oxidized products.

7. A bio-metallurgical process for bio-oxidizing in ore metal sulfides to sulphates, sulphur to sulphate, uranous oxide to uranic oxide or ferrous iron to ferric iron, comprising the steps of:

a) treating an ore with an acidic solution in an amount sufficient to prevent compaction of said ore and to provide an acidity suitable for the growth of microorganisms obtained from ore or derived from microorganisms obtained from ore, and reducing the volume of said acidic solution by adding an agent selected from the group consisting of wetting agents, tensoactive agents, detergents and surfactants, which microorganisms are capable of bio-oxidizing metal sulfides, sulphur, uranous oxide and/or ferrous iron;

b) adding to said ore a microbial inoculum containing said microorganisms;

c) adding to said treated and inoculated ore a dehydrating agent to effect removal of water, until a moisture content below a supersaturated moisture is obtained and until soluble bio-oxidized products in solid state and containing colonies of said microorganisms are obtained;

d) maintaining said ore at a temperature within the growth range temperature of said microorganisms until said bio-oxidation is completed; and e) separating out said soluble bio-oxidized products.

8. A bio-metallurgical process for bio-oxidizing in ore metal sulfides to sulphates, sulphur to sulphate, uranous oxide to uranic oxide or ferrous iron to ferric iron, comprising the steps of:

a) treating an ore with an acidic solution in an amount sufficient to prevent compaction of said ore and to provide an acidity suitable for the growth of microorganisms obtained from ore or derived from microorganisms obtained from ore, which microorganisms are capable of bio-oxidizing metal sulfides, sulphur, uranous oxide and/or ferrous iron;

b) adding to said ore a microbial inoculum containing said microorganisms;

c) effecting removal of water from said treated and inoculated ore until a moisture content below a supersaturated moisture is obtained and until soluble bio-oxidized products in solid state and containing colonies of said microorganisms are obtained;

d) maintaining said ore at a temperature within the growth range temperature of said microorganisms until said bio-oxidation is completed;

wherein water activity or thermodynamically available water is decreased in order to accelerate said bio-oxidation in step (c) or steps (c) and (d) by adding to said acidic solution in step (a) a dehydrating agent selected from the group consisting of polyols, glycols, esters of glycols, ethers of glycols, polyglycols, polyglycol esters, polyglycol ethers, heavy metal sulphates, calcium salts, magnesium salts, silicic acid, sodium silicate, sulphuric anhydride, or a mixture thereof; and e) separating out said soluble bio-oxidized products.

9. A bio-metallurgical process for bio-oxidizing in ore metal sulfides to sulphates, sulphur to sulphate, uranous oxide to uranic oxide or ferrous iron to ferric iron, comprising the steps of:

a) treating an ore with an acidic solution in an amount sufficient to prevent compaction of said ore and to provide an acidity suitable for the growth of microorganisms present in said ore, which microorganisms are capable of bio-oxidizing metal sulfides, sulphur, uranous oxide and/or ferrous iron;

b) effecting removal of water from said treated ore until a moisture content below a supersaturated moisture is obtained and until soluble bio-oxidized products in solid state and containing colonies of said microorganisms are obtained;

c) maintaining said ore at a temperature within the growth range temperature of said microorganisms until said bio-oxidation is completed;

d) repeating steps a), b) and c) in a cyclical manner until a desired yield of soluble bio-oxidation product in solid state is obtained, wherein water activity or thermodynamically available water is decreased in order to accelerate said bio-oxidation in step (b) or steps (b) and (c) by adding to said acidic solution in step (a) a dehydrating agent selected from the group consisting of polyols, glycols, esters of glycols, ethers of glycols, polyglycols, polyglycol esters, polyglycol ethers, heavy metal sulphates, calcium salts, magnesium salts, silicic acid, sodium silicate, sulphuric anhydride, or a mixture thereof; and e) separating out said soluble bio-oxidized products.

10. A bio-metallurgical process for bio-oxidizing in ore metal sulfides to sulphates, sulphur to sulphate, uranous oxide to uranic oxide or ferrous iron to ferric iron, comprising the steps of:

a) treating an ore with an acidic solution in an amount sufficient to prevent compaction of said ore and to provide an acidity suitable for the growth of microorganisms obtained from ore or derived from microorganisms obtained from ore, which microorganisms are capable of bio-oxidizing metal sulfides, sulphur, uranous oxide and/or ferrous iron;

b) adding to said ore a microbial inoculum containing said microorganisms;

c) pelletizing said ore after steps (a) and/or (b), wherein said ore is pelletized around solid inert elements selected from the group consisting of triturated rocks, triturated quartz, gravel, glass elements, plastic elements, and rubber elements;

d) effecting removal of water from said treated and inoculated ore until a moisture content below a supersaturated moisture is obtained and until soluble bio-oxidized products in solid state and containing colonies of said microorganisms are obtained;

e) maintaining said ore at a temperature within the growth range temperature of said microorganisms until said bio-oxidation is completed; and f) separating out said soluble bio-oxidized products.

11. A bio-metallurgical process for bio-oxidizing in ore metal sulfides to sulphates, sulphur to sulphate, uranous oxide to uranic oxide or ferrous iron to ferric iron, comprising the steps of:

a) treating an ore with an acidic solution in an amount sufficient to prevent compaction of said ore and to provide an acidity suitable for the growth of microorganisms obtained from ore or derived from microorganisms obtained from ore, which microorganisms are capable of bio-oxidizing metal sulfides, sulphur, uranous oxide and/or ferrous iron;

b) adding to said ore a microbial inoculum containing said microorganisms;

c) pelletizing said ore after steps (a) and/or (b), wherein said ore is pelletized around solid inert elements selected from the group consisting of triturated rocks, triturated quartz, gravel, glass elements, plastic elements, and rubber elements;

d) adding to said treated and inoculated ore a dehydrating agent to effect removal of water, until a moisture content below a supersaturated moisture is obtained and until soluble bio-oxidized products in solid state and containing colonies of said microorganisms are obtained;

e) maintaining said ore at a temperature within the growth range temperature of said microorganisms until said bio-oxidation is completed; and f) separating out said soluble bio-oxidized products.

12. A bio-metallurgical process for bio-oxidizing in ore metal sulfides to sulphates, sulphur to sulphate, uranous oxide to uranic oxide or ferrous iron to ferric iron comprising the steps of:

a) treating an ore with an acidic solution in an amount sufficient to prevent compaction of said ore and to provide an acidity suitable for the growth of microorganisms present in said ore, which microorganisms are capable of bio-oxidizing metal sulfides, sulphur, uranous oxide and/or ferrous iron;

b) pelletizing said ore around solid inert elements selected from the group consisting of triturated rocks, triturated quartz, gravel, glass elements, plastic elements and rubber elements;

c) effecting removal of water from said treated ore until a moisture content below a supersaturated moisture is obtained and until soluble bio-oxidized products in solid state and containing colonies of said microorganisms are obtained;

d) maintaining said ore at a temperature within the growth range temperature of said microorganisms until said bio-oxidation is completed;

e) repeating steps a), b) , c) and d) in a cyclical manner until a desired yield of soluble bio-oxidation product in solid state is obtained; and f) separating out said soluble bio-oxidized products.

* * * * *